US006797807B1

(12) United States Patent
Blaschuk et al.

(10) Patent No.: US 6,797,807 B1
(45) Date of Patent: Sep. 28, 2004

(54) COMPOUNDS AND METHODS FOR CANCER THERAPY

(75) Inventors: Orest W. Blaschuk, Westmount (CA); James Matthew Symonds, Ottawa (CA); Barbara J. Gour, Kemptville (CA); J. Steven Alexander, Shreveport, LA (US)

(73) Assignee: Adherex Technologies, Inc., Ottawa (CA)

( * ) Notice: Subject to any disclaimer, the term of this patent is extended or adjusted under 35 U.S.C. 154(b) by 0 days.

(21) Appl. No.: 09/450,073

(22) Filed: Nov. 29, 1999

Related U.S. Application Data

(63) Continuation-in-part of application No. 09/222,373, filed on Dec. 29, 1998, now Pat. No. 6,110,747, which is a continuation-in-part of application No. 09/001,511, filed on Dec. 31, 1997, now Pat. No. 6,248,864.

(51) Int. Cl.$^7$ ............................................. A61K 38/00
(52) U.S. Cl. ..................... 530/300; 530/317; 530/324; 530/325; 530/326; 530/327; 530/328; 530/329; 530/330; 530/387; 514/12; 514/13; 514/14; 514/15; 514/16; 514/17; 514/18; 514/19; 424/185.1; 436/512
(58) Field of Search ............................. 514/12, 13, 14, 514/15, 16, 18, 19, 17; 530/300, 317, 324, 325, 326, 327, 328, 329, 330, 387; 424/185.1; 436/512

(56) References Cited

U.S. PATENT DOCUMENTS 6,110,747 A  *  8/2000  Blaschuk et al. ............ 436/512
6,248,864 B1 *  6/2001  Blaschuk et al. ............ 530/317

FOREIGN PATENT DOCUMENTS

| EP | 831 148 A1 | 3/1998 |
| JP | WO 97/32982 | 9/1997 |
| WO | WO 97/33605 | 9/1997 |
| WO | WO 98/21237 | 5/1998 |

OTHER PUBLICATIONS

Golden, Frederic, "Of Mice and Men: Don't Blame the Rodents" Time, pp. 40–46. May 1998.*
Gura, Trisha "Systems for Identifying New Drugs Are Often Faulty" Science, vol. 278, 1041–1042, Nov. 1997.*
Dermer, Gerald "Another Anniversary for the War on Cancer", Biotechnology, vol. 12, p. 320. Mar. 1994.*
Ando–Akatsuka et al., "Interspecies Diversity of the Occludin Sequence: cDNA Cloning of Human, Mouse, Dog, and Rat–Kangaroo Homologues," *The Journal of Cell Biology* 133(1): 43–47, 1996.

Chen et al., "Cooh Terminus of Occludin Is Required for Tight Junction Barrier Function in Early *Xenopus* Embryos," *The Journal of Cell Biology* 138(4): 891–899, 1997.

Furuse et al., "Overexpression of occludin, a tight junction–associated integral membrane protein, induces the formation of intracellular multilamellar bodies bearing tight junction–like structures," *Journal of Cell Science* 109: 429–435, 1996.

Furuse et al., "Occludin: A Novel Integral Membrane Protein Localizing at Tight Junctions," *The Journal of Cell Biology* 123(No. 6, Part 2): 1777–1788, 1993.

Lampugnani and Dejana, "Interendothelial junctions: structure, signalling and functional roles," *Current Opinion in Cell Biology* 9: 674–682, 1997.

Pique et al., "Among All Human T–Cell Leukemia Virus Type 1 Proteins, Tax, Polymerase, and Envelope Proteins Are Predicted as Preferential Targets for the HLA–A2–Restricted Cytotoxic T–Cell Response," *Journal Of Virology* 70(8):4919–4926, 1996.

Wong and Gumbiner, "A Synthetic Peptide Corresponding to the Extracellular Domain of Occludin Perturbs the Tight Junction Permeability Barrier," *Journal of Cell Biology* 136(2): 399–409, 1997.

Jaeger et al., "Small Synthetic Peptides Homologous To Segments Of Occludin Impair Tight Junction Resealing In A $Ca^{+2}$ Switch Assay In A6 Cell Monolayers," *Mol. Biol. Cell.* (Suppl.8):205A, Abstract No. 1189, 1997.

Lacaz–Vieira et al., "Small Synthetic Peptides Homologous To Segments Of the First External Loop of Occludin Impair Tight Junction Resealing," *J. Membrane Biol.* 168:289–297, 1999.

* cited by examiner

*Primary Examiner*—Brenda Brumback
*Assistant Examiner*—Anish Gupta
(74) *Attorney, Agent, or Firm*—Seed IP Law Group PLLC

(57) ABSTRACT

Methods for using modulating agents to enhance or inhibit occludin-mediated cell adhesion in a variety of in vivo and in vitro contexts are provided. Within certain embodiments, the modulating agents may be used for cancer therapy or to increase immune cell infiltration into tumors. The modulating agents comprise at least one occludin cell adhesion recognition sequence or an antibody or fragment thereof that specifically binds the occludin cell adhesion recognition sequence. Modulating agents may additionally comprise one or more cell adhesion recognition sequences recognized by the other adhesion molecules. Such modulating agents may, but need not, be linked to a targeting agent, drug and/or support material.

21 Claims, 17 Drawing Sheets

```
Dog         GVNPTAQA--SGSLYSSQIYAMCNQFYASTATGLYMDQYLYHYCVVDPQE
Human       GVNPTAQS--SGSLYGSQIYALCNQFYTPAATGLYVDDQYLYHYCVVDPQE
Mouse       GVNPTAQA--SGSMYGSQIYMICNQFYTPGGTGLYVDDQYLYHYCVVDPQE
Rat-kangaroo GVNPRAGLGASSGSLYYNQMLMLCNQMMSPVAGG-IMNQYLYHYCMVDPQE Consensus   GVNPtAqxgasSGSlYxsQiyxxCNQfyxpxatGlyxdQYLYHYCvVDPQE
```

Fig. 2

H-KLYHYD-OH

H-KLYQYD-OH

H-CYLYHYC-OH

H-CYLYQYC-OH

YLYHY

YLYQY

QYLYHY

QYLYHY

H-CLYHYC-OH

H-CLYQYC-OH

Ac-N-CLYHYC-OH

Ac-N-CLYQYC-OH

Peptide 3 (100μg/mL)

Control

COMPOUNDS AND METHODS FOR CANCER THERAPY

CROSS-REFERENCE TO RELATED APPLICATION

This application is a continuation-in-part of U.S. application Ser. No. 09/222,373, filed Dec. 29, 1998, and now U.S. Pat. No. 6,110,747, which is a continuation-in-part of U.S. application Ser. No. 09/001,511, filed Dec. 31, 1997 and now U.S. Pat. No. 6,248,864.

TECHNICAL FIELD

The present invention relates generally to methods for regulating occludin-mediated processes, and more particularly to the use of modulating agents comprising an occludin cell adhesion recognition sequence and/or an antibody that specifically recognizes such a sequence for inhibiting functions such as cell adhesion and the formation of tissue permeability barriers.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions, spot desmosomes and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., *In: Cell Adhesion and Invasion in Cancer Metastasis*, P. Brodt, ed., pp. 17–34, RG Landes Co.(Austin Tex., 1996). The cadherins (abbreviated CADs) are membrane glycoproteins that generally promote cell adhesion through homophilic interactions (a CAD on the surface of one cell binds to an identical CAD on the surface of another cell). Cadherins have been shown to regulate epithelial, endothelial, neural and cancer cell adhesion, with different CADs expressed on different cell types. For example, N (neural)—cadherin is predominantly expressed by neural cells, endothelial cells and a variety of cancer cell types. E (epithelial)—cadherin is predominantly expressed by epithelial cells. VE (vascular endothelial)—cadherin is predominantly expressed by endothelial cells. Other CADs are P (placental)—cadherin, which is found in human skin, and R (retinal)—cadherin. A detailed discussion of the cadherins is provided in Munro S B et al., 1996, *In: Cell Adhesion and Invasion in Cancer Metastasis*, P. Brodt, ed., pp. 17–34 (RG Landes Company, Austin Tex.) and Lampugnani and Dejana, *Curr. Opin. Cell Biol.* 9:674–682, 1997.

CAD-mediated cell adhesion triggers a cascade of events that lead to the formation of intercellular junctions, and ultimately to the establishment of permeability barriers between tissue compartments. The intercellular junction that is directly responsible for the creation of permeability barriers that prevent the diffusion of solutes through paracellular spaces is known as the tight junction, or zonula occludens (Anderson and van Itallie, *Am. J. Physiol.* 269:G467–G475, 1995; Lampugnani and Dejana, *Curr. Opin. Cell Biol.* 9:674–682, 1997).

Occludin is a transmembrane component of tight junctions (Furuse et al., *J. Cell Biol.* 123:1777–1788, 1993; Furuse et al., *J. Cell Sci.* 109:429–435, 1996). This protein appears to be expressed by all endothelial cell types, as well as by most epithelial cell types. Occludin is an integral membrane protein (FIG. 1) that is composed of two extracellular domains (EC1 and EC2), four hydrophobic domains (TM1–TM4) that transverse the plasma membrane, and three cytoplasmic domains (CP1–CP3). The structures of all known mammalian occludins are similar (FIG. 2; Ando-Akatsuka et al., *J. Biol. Chem.* 133:43–47, 1996). Occludin is believed to be directly involved in cell adhesion and the formation of tight junctions (Furuse et al., *J. Cell Sci.* 109:429–435, 1996; Chen et al., *J. Cell Biol.* 138:891–899, 1997). It has been proposed that occludin promotes cell adhesion through homophilic interactions (an occludin on the surface of one cell binds to an identical occludin on the surface of another cell). A detailed discussion of occludin structure and function is provided by Lampugnani and Dejana, *Curr. Opin. Cell Biol.* 9:674–682, 1997.

Although cell adhesion is required for certain normal physiological functions, there are situations in which the level of cell adhesion is undesirable. For example, many pathologies (such as autoimmune diseases and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects.

Further, internal barriers developed by tumors inhibit the immune system's ability to attack tumor cells. Immune cells such as leukocytes often cannot infiltrate a tumor, and thus tumor cells are protected from the body's natural defenses. There are presently no available methods for enhancing immune cell infiltration of solid tumors.

Accordingly, there is a need in the art for compounds that modulate cell adhesion, improve drug delivery across permeability barriers and permit immune cell infiltration of solid tumors. The present invention fulfills this need and further provides other related advantages.

SUMMARY OF THE INVENTION

The present invention provides compounds and methods for modulating occludin-mediated cell adhesion and the formation of permeability barriers. Within certain aspects, compounds provided herein comprise an occludin CAR sequence, or variant thereof that retains the ability to modulate occludin-mediated cell adhesion. Certain compounds are cyclic peptides that comprise the sequence LYHY (SEQ ID NO:1). Within certain embodiments, such cyclic peptides have the formula:

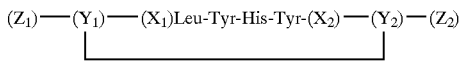

wherein $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may comprise modifications such as an N-acetyl or N-alkoxybenzyl group and/or a C-terminal amide or ester group. Cyclic peptides may be cyclized via, for example, a disulfide bond; an amide bond between terminal functional groups, between residue side-chains or between one terminal functional group and one residue side chain; a thioether bond or $\delta_1\delta_1$-ditryptophan, or a derivative thereof.

Within other embodiments, such compounds may be linear peptides comprising the sequence LYHY (SEQ ID NO:1) or a variant thereof. Such peptides are preferably 4–30 amino acid residues in length, preferably 5–16 amino acid residues, and more preferably 6–9 amino acid residues.

Within further aspects, the present invention provides cell adhesion modulating agents that comprise a cyclic or linear peptide as described above. Within specific embodiments, such modulating agents may be linked to one or more of a targeting agent, a drug, a solid support or support molecule, or a detectable marker. Within further specific embodiments, cell adhesion modulating agents are provided that comprise a sequence selected from the group consisting of QYLYHYCVVD (SEQ ID NO:2), YLYHYCVVD (SEQ ID NO:12), LYHYCVVD (SEQ ID NO:13), QYLYHYC (SEQ ID NO:14), YLYHYC (SEQ ID NO:15), LYHYC (SEQ ID NO:16), QYLYHY (SEQ ID NO:17), YLYHY (SEQ ID NO:18) and derivatives of the foregoing sequences having one or more C-terminal, N-terminal and/or side chain modifications.

Within further related aspects, cell adhesion modulating agents are provided which comprise an antibody or antigen-binding fragment thereof that specifically binds to a cell adhesion recognition sequence bound by an occludin.

In addition, any of the above cell adhesion modulating agents may further comprise one or more of: (a) a cell adhesion recognition sequence that is bound by an adhesion molecule other than an occludin, wherein said cell adhesion recognition sequence is separated from any LYHY (SEQ ID NO:1) sequence(s) by a linker; and/or (b) an antibody or antigen-binding fragment thereof that specifically binds to a cell adhesion recognition sequence bound by an adhesion molecule other than an occludin.

The present invention further provides pharmaceutical compositions comprising a cell adhesion modulating agent as described above, in combination with a pharmaceutically acceptable carrier. Such compositions may further comprise a drug. In addition, or alternatively, such compositions may further comprise one or more of: (a) a peptide comprising a cell adhesion recognition sequence that is bound by an adhesion molecule other than an occludin; and/or (b) an antibody or antigen-binding fragment thereof that specifically binds to a cell adhesion recognition sequence bound by an adhesion molecule other than an occludin.

Within further aspects, methods are provided for modulating cell adhesion, comprising contacting a cadherin-expressing cell with a cell adhesion modulating agent as described above.

The present invention further provides methods for enhancing the delivery of a drug to a tumor in a mammal, comprising administering to a mammal a cell adhesion modulating agent as provided above and a drug, wherein the modulating agent inhibits occludin-mediated cell adhesion.

Within further aspects, the present invention provides methods for treating cancer in a mammal, comprising administering to a mammal a cell adhesion modulating agent as provided above, wherein the modulating agent inhibits occludin-mediated cell adhesion.

Within further aspects, the present invention provides methods for enhancing immune cell infiltration of a tumor in a mammal, comprising administering to a mammal a cell adhesion modulating agent as provided above, wherein the modulating agent inhibits occludin-mediated cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of representative mammalian occludin EC2 domains: human (SEQ ID NO:5), mouse (SEQ ID NO:6), dog (SEQ ID NO:7), and rat-kangaroo (SEQ ID NO:8), as indicated, along with the consensus sequence obtained using a Clustal W protein sequence alignment. The occludin cell adhesion recognition sequence, LYHY (Leu-Tyr-His-Tyr; SEQ ID NO:1), along with flanking amino acid residues is shown in bold.

FIG. 4B).

FIG. 12B shows the gaps between adjacent endothelial cells and the lack of junctional proteins at these gaps (arrows). Bar=25 µm.

DETAILED DESCRIPTION OF THE INVENTION

Figure 1:
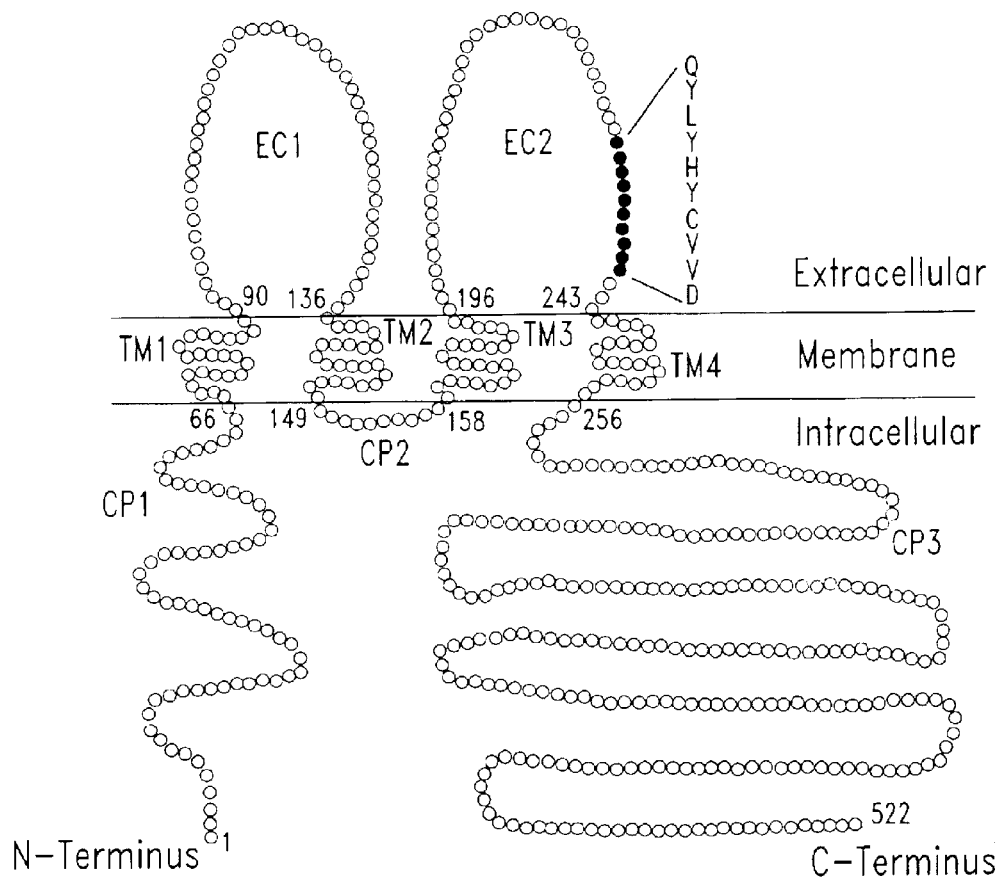
FIG. 1 is a diagram depicting the structure of a human occludin. The two extracellular domains are designated EC1 and EC2, the four hydrophobic domains that transverse the plasma membrane are represented by TM1–TM4, and the three cytoplasmic domains are denoted CP1–CP3. The occludin cell adhesion recognition sequence, LYHY (Leu-Tyr-His-Tyr; SEQ ID NO:1), along with flanking amino acid residues is shown within EC2 and is indicated by •.
Figure 3A:
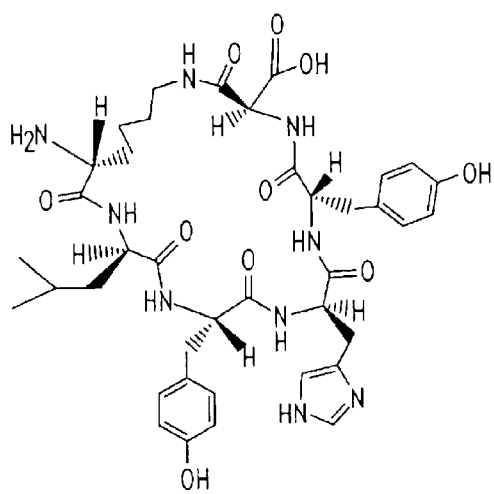
FIGS. 3A–3E provide the structures of representative cyclic peptide modulating agents.
Figure 3A:
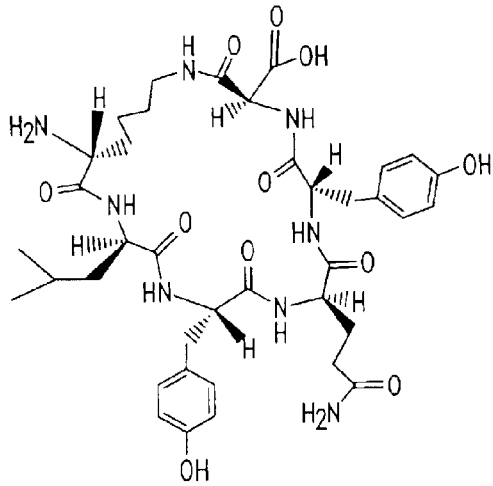
Figure 3A:
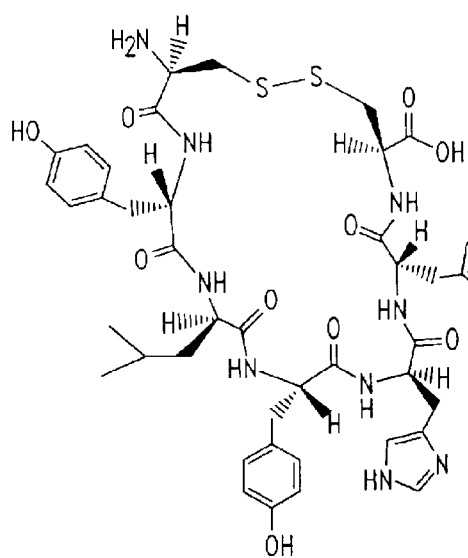
Figure 3A:
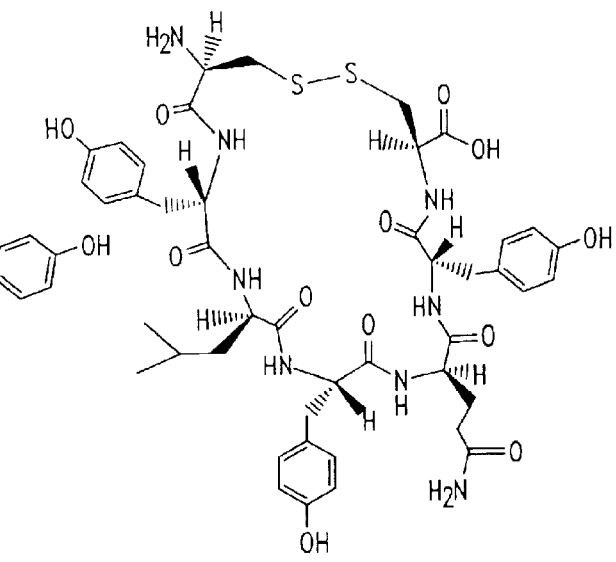
Figure 3B:
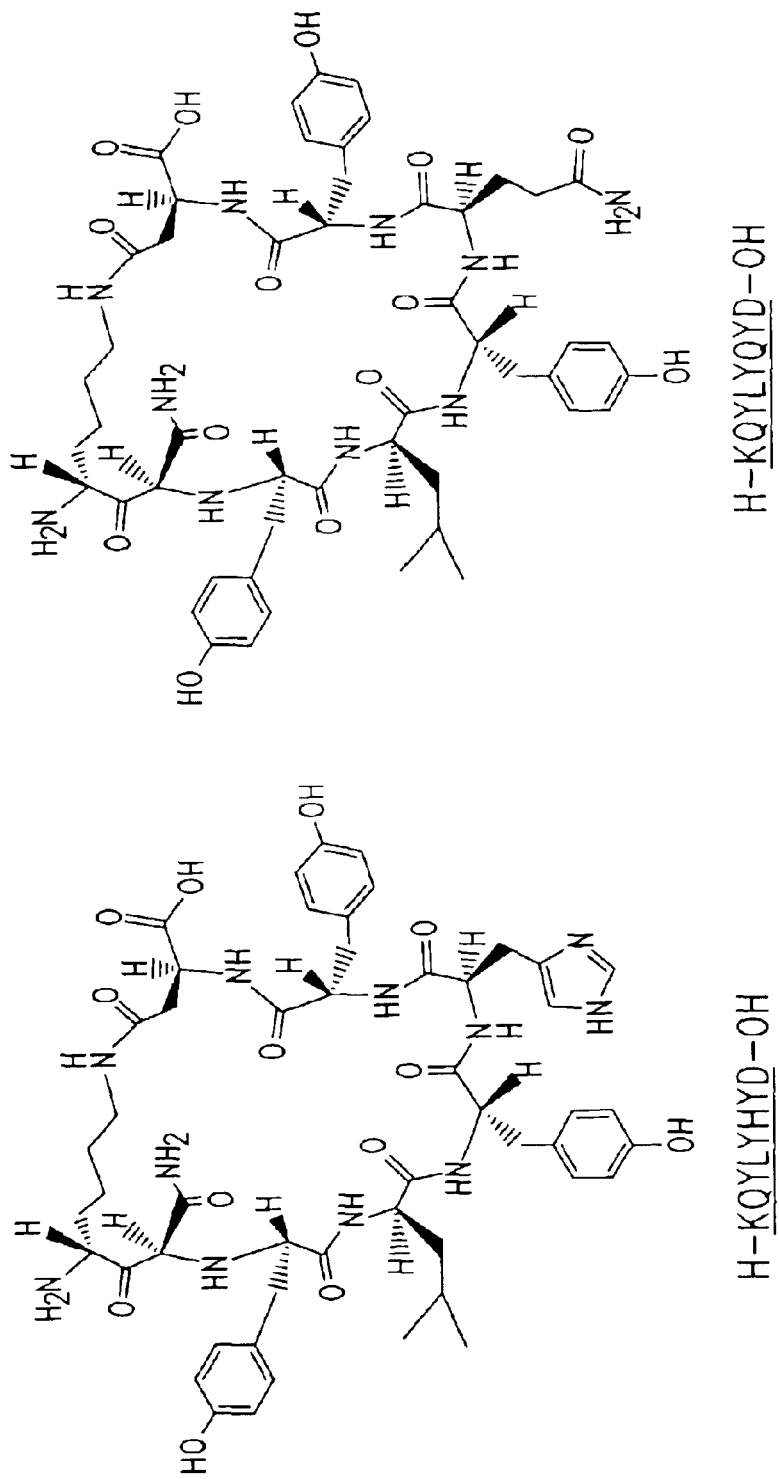
Figure 3C:
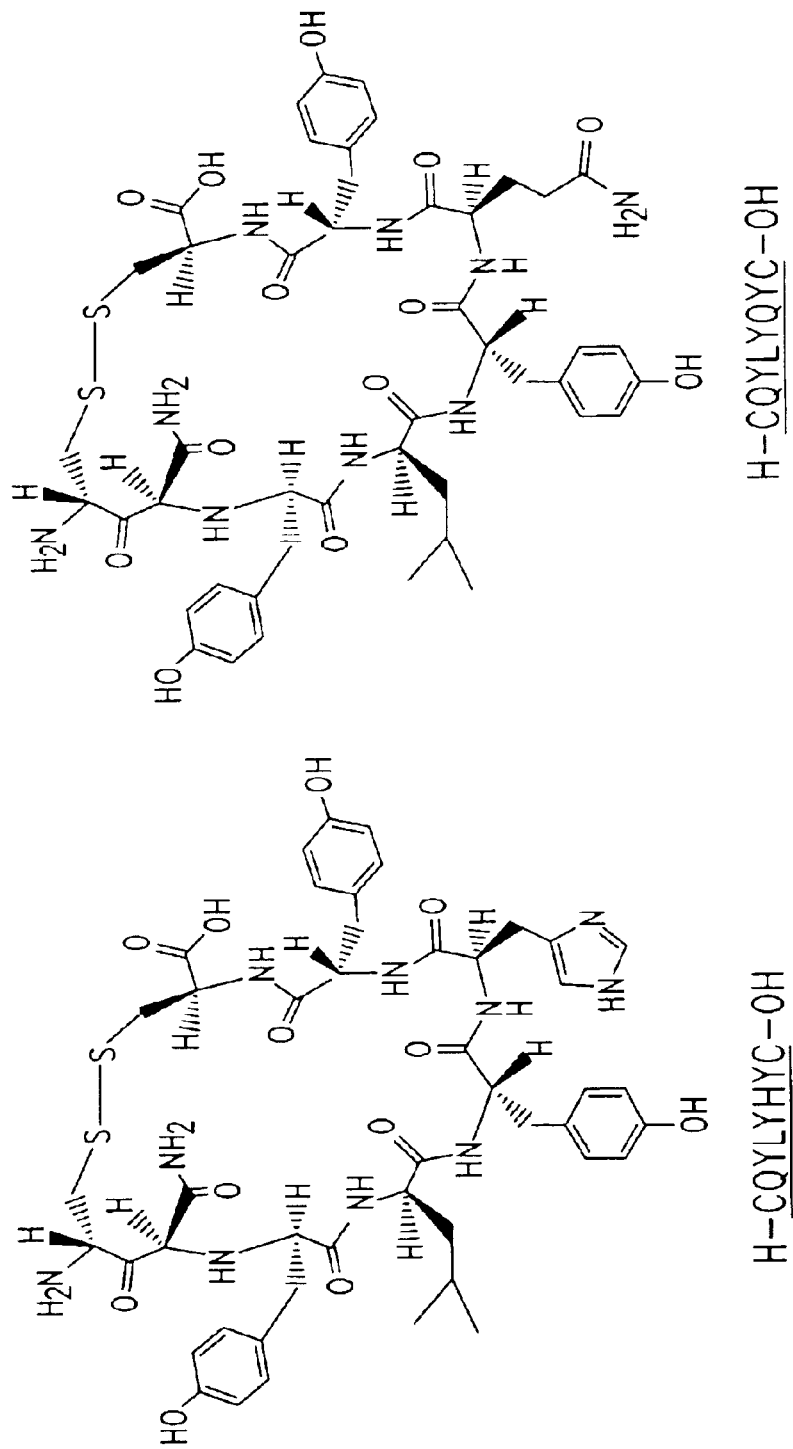
Figure 3D:
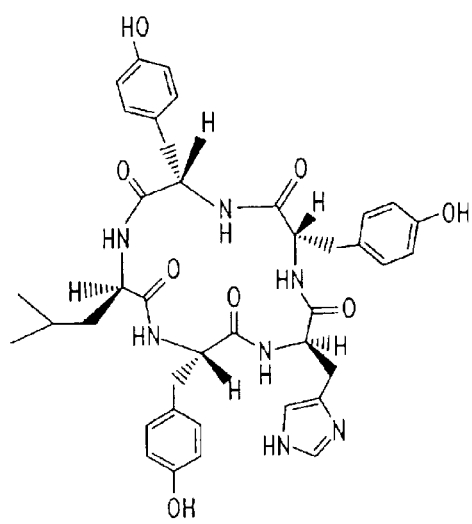
Figure 3D:
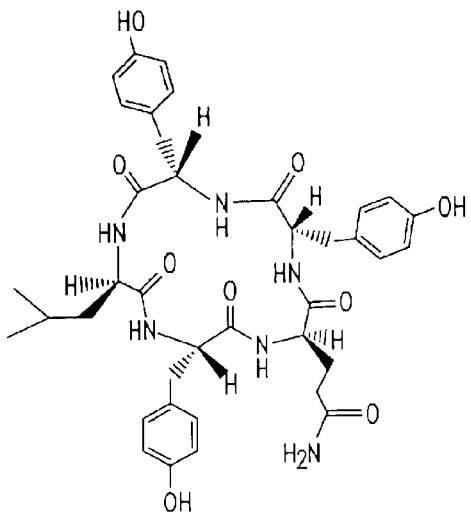
Figure 3D:
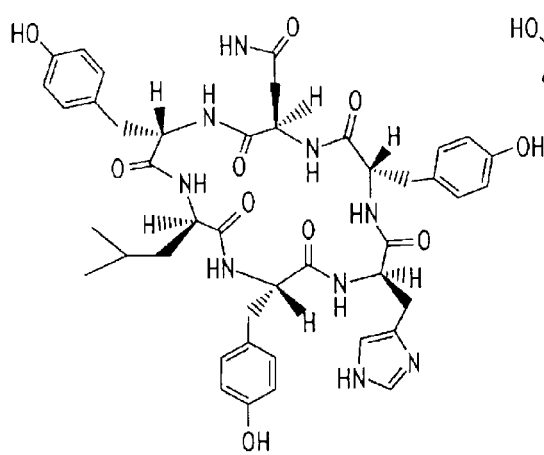
Figure 3D:
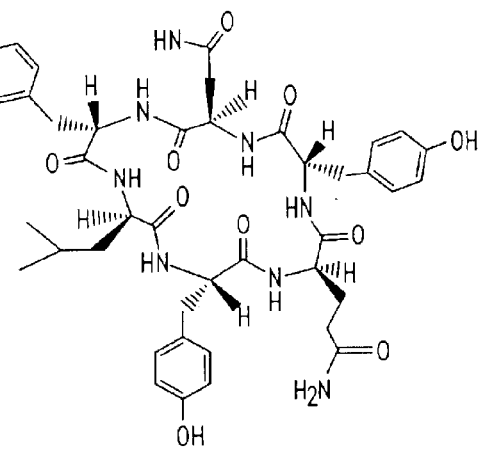
Figure 3E:
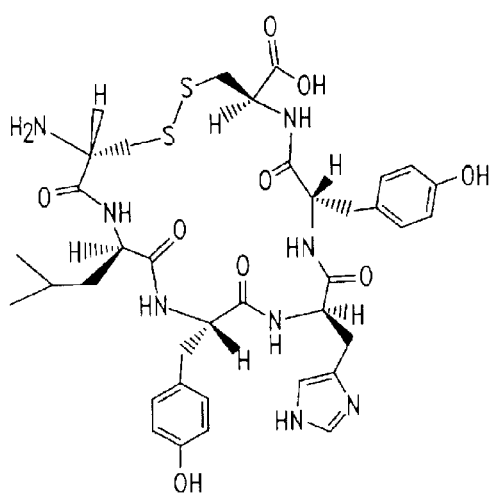
Figure 3E:
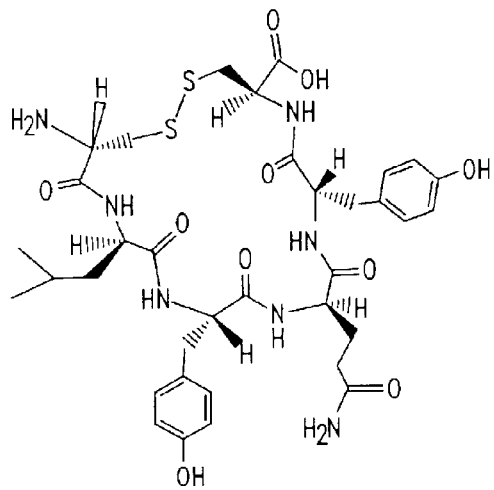
Figure 3E:
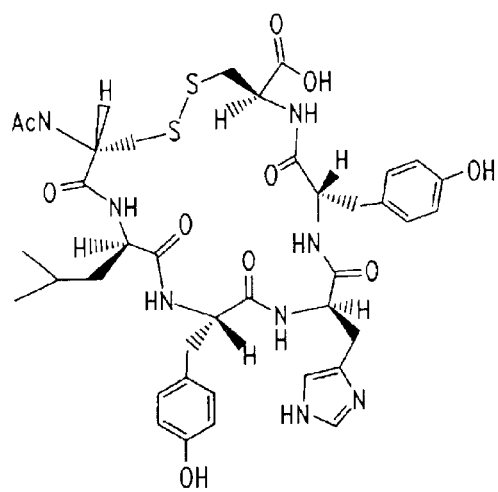
Figure 3E:
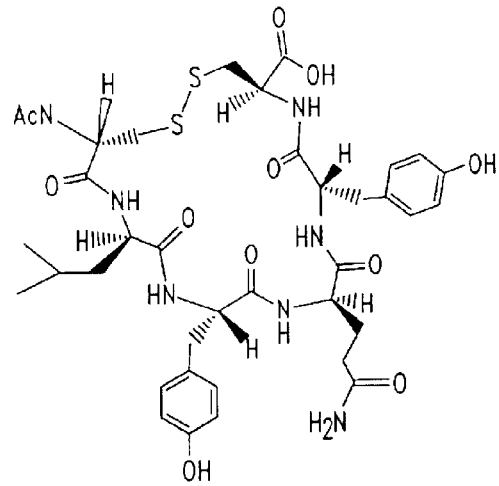

As noted above, the present invention provides cell adhesion modulating agents comprising peptides that are capable of modulating occludin-mediated processes, such as cell adhesion. In general, to modulate occludin-mediated cell adhesion, an occludin-expressing cell is contacted with a cell adhesion modulating agent (also referred to herein as a "modulating agent") either in vivo or in vitro. It has been found, within the context of the present invention, that the second extracellular domain (EC2) of occludin contains a CAR sequence that promotes the formation of permeability barriers. Accordingly, a modulating agent may comprise at least one peptide (which may, but need not, be cyclic) that contains an occludin cell adhesion recognition (CAR) sequence and/or an antibody or fragment thereof that specifically binds to an occludin CAR sequence. In humans and certain other mammals, the CAR sequence is LYHY (Leu-Tyr-His-Tyr; SEQ ID NO:1; see FIG. 2 and SEQ ID NOs:5–8). However, the present invention further contemplates occludin CAR sequences from other organisms. Such CAR sequences may be identified based upon sequence similarity to the sequences provided herein, and the ability to modulate an occludin-mediated function may be confirmed as described herein. A modulating agent may further comprise one or more additional CAR sequences and/or antibodies (or antigen-binding fragments thereof) that specifically bind to an occludin CAR sequence. Alternatively, or in addition, a modulating agent may further comprise one or more CAR sequences for a CAM other than an occludin and/or an antibody or antigen-binding fragment thereof that specifically binds to such a CAM.

Certain modulating agents described herein inhibit cell adhesion. Such modulating agents may generally be used, for example, to treat diseases or other conditions characterized by undesirable cell adhesion or to facilitate drug delivery to a specific tissue or tumor. Within other aspects of the present invention, certain modulating agents may be used to enhance cell adhesion (e.g., to supplement or replace stitches or to facilitate wound healing). Certain modulating agents provided herein have the ability to stimulate the formation of tight junctions in epithelial cells, but not in endothelial cells. Such agents may be used, for example, for treating diarrhea.

Cell Adhesion Modulating Agents

The term "cell adhesion modulating agent," as used herein, refers to a molecule comprising at least one of the following components:

(a) a linear or cyclic peptide sequence that is at least 50% identical to an occludin CAR sequence (i.e., an occludin CAR sequence or an analogue thereof that retains at least 50% sequence identity);

(b) a mimetic (e.g., peptidomimetic or small molecule mimic) of an occludin CAR sequence;

(c) a substance, such as an antibody or antigen-binding fragment thereof, that specifically binds an occludin CAR sequence; and/or (d) a polynucleotide encoding a polypeptide that comprises an occludin CAR sequence or analogue thereof.

A modulating agent may consist entirely of one or more of the above elements, or may additionally comprise further peptide and/or non-peptide regions. Additional peptide or polynucleotide regions may be derived from occludin (preferably an extracellular domain that comprises a CAR sequence) and/or may be heterologous. Certain modulating agents comprise the occludin CAR sequence LYHY (SEQ ID NO:1) or an analogue thereof. Within certain preferred embodiments, such a modulating agent contains 4–30 consecutive amino acid residues, preferably 5–16 consecutive amino acid residues and more preferably 6–9 consecutive amino acid residues, present within an occludin.

An "occludin CAR sequence," as used herein, refers to an amino acid sequence that is present within in a naturally occurring occludin and that is capable of detectably modulating an occludin-mediated function, such as cell adhesion, as described herein. In other words, contacting an occludin-expressing cell with a peptide comprising a CAR sequence results in a detectable change in an occludin-mediated function using at least one of the representative assays provided herein. CAR sequences may be of any length, but generally comprise 4–16 amino acid residues, and preferably 5–8 amino acid residues. As noted above, the four amino acid sequence LYHY (SEQ ID NO:1) is an occludin CAR sequence.

As an alternative to comprising a native occludin CAR sequence, modulating agents as described herein may comprise an analogue or mimetic of an occludin CAR sequence. Within the specific embodiments described herein, it should be understood that an analogue or mimetic may be substituted for a native CAR sequence within any modulating agent. An analogue generally retains at least 50% identity to a native occludin CAR sequence, and modulates an occludin-mediated function as described herein. Such analogues preferably contain at least three residues of, and more preferably at least five residues of, an occludin CAR sequence. An analogue may contain any of a variety of amino acid substitutions, additions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of an occludin CAR sequence analogue is the ability to modulate an occludin-mediated function, which may be evaluated using the representative assays provided herein.

Alternatively, a modulating agent may comprise one or more bioisoteres. "Bioisoteres" are substituents or groups that have chemical or physical similarities and which produce broadly similar biological properties. For example, preferred substitutions for the imidazole ring of histidine in the aforementioned modulators are triazole, pyrazole, thiatriazole, triazolone, benzoxadiazole, pyrazine, pyrimidine, oxadiazole, tetraazole, aminopyridine, triazine, benzodioxole, benzodiazole or benzoxadiazole.

A mimetic is a non-peptidyl compound that is conformationally similar to an occludin CAR sequence, such that it modulates an occludin-mediated function as described below. Such mimetics may be designed based on techniques that evaluate the three dimensional structure of the peptide. For example, Nuclear Magnetic Resonance spectroscopy (NMR) and computational techniques may be used to determine the conformation of an occludin CAR sequence within a cyclic peptide. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the occludin CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation, ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as —$CH_2NH$—, —CSNH—, —$CH_2S$—, —CH=CH—, —$CH_2CH_2$—, —CONMe— and others. These backbone amide linkages can also be part of a ring structure (e.g., lactam). Mimetics may be designed where one or more of the side chain functionalities of the occludin CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of the CAR sequence. It should be understood that, within embodiments described below, an analogue or mimetic may be substituted for an occludin CAR sequence.

A portion of a modulating agent that comprises an occludin CAR sequence, or analogue or mimetic thereof, may be a linear or cyclic peptide. The term "cyclic peptide," as used herein, refers to a peptide or salt thereof that comprises (1) an intramolecular covalent bond between two non-adjacent residues and (2) at least one occludin CAR sequence. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds.

In addition to one or more of the above components, a modulating agent may comprise one or more additional CAR sequences, which may or may not be occludin CAR sequences, and/or one or more antibodies or fragments thereof that specifically recognize a CAR sequence. Additional CAR sequences may be present within a cyclic peptide containing an occludin CAR sequence, within a separate cyclic peptide component of the modulating agent and/or in a non-cyclic portion of the modulating agent.

Antibodies and antigen-binding fragments thereof are typically present in a non-cyclic portion of the modulating agent.

Within certain embodiments in which inhibition of cell adhesion is desired, a modulating agent may contain one occludin CAR sequence or analogue thereof. Alternatively, such an agent may comprise multiple occludin CAR sequences, which may be adjacent to one another (i.e., without intervening sequences) or in close proximity (i.e., separated by peptide and/or non-peptide linkers to give a distance between the CAR sequences that ranges from about 0.1 to 400 nm). For example, a modulating agent with adjacent LYHY sequences may comprise the peptide LYHY-LYHY (SEQ ID NO:9). A representative modulating agent with LYHY sequences in close proximity may comprise the sequence QLYHYQLYHYQLYHY (SEQ ID NO:10). One or more antibodies, or fragments thereof, may similarly be used within such embodiments, either alone or in combination with one or more CAR sequences.

In certain embodiments, a modulating agent as described above may enhance cell adhesion among epithelial cells, but not among endothelial cells. It has been found, within the context of the present invention, that certain modulating agents comprising an LYHY sequence affect endothelial and epithelial cells differently, stimulating the formation of tight junctions in epithelial cells. Such agents include H-QYLYHYCVVD-COOH (SEQ ID NO:2) and N-Ac-CLYHYC-NH$_2$ (SEQ ID NO:3). Terminal functional groups may influence the activity of peptide modulating agents in epithelial and endothelial cells.

Within other embodiments in which enhancement of cell adhesion is desired, a modulating agent may generally contain multiple occludin CAR sequences and/or antibodies that specifically bind to such sequences, joined by linkers as described above. Enhancement of cell adhesion may also be achieved by attachment of multiple modulating agents to a support molecule or material, as discussed further below.

A modulating agent as described herein may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the LYHY sequence(s) and/or each other. Such modulating agents may generally be used within methods in which it is desirable to simultaneously disrupt cell adhesion mediated by multiple adhesion molecules. As used herein, an "adhesion molecule" is any molecule that mediates cell adhesion via a receptor on the cell's surface. Adhesion molecules include classical cadherins; atypical cadherins such as cadherin-11 (OB cadherin), cadherin-5 (VE-cadherin), cadherin-6 (K-cadherin), cadherin-7, cadherin-8, cadherin-12 (Br-cadherin, cadherin-14, cadherin-15, and PB-cadherin; other nonclassical cadherins such as desmocollins (dsc) and desmogleins (dsg); claudin; integrins; and members of the immunoglobulin supergene family, such as N-CAM and PECAM). Preferred CAR sequences for inclusion within a modulating agent include: (a) His-Ala-Val (HAV), which is bound by classical cadherins; (b) Arg-Gly-Asp (RGD), which is bound by integrins (see Cardarelli et al., *J. Biol. Chem.* 267:23159–23164, 1992); (c) KYSFNYDGSE (SEQ ID NO:11), which is bound by N-CAM; (d) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:47), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (e) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO:48), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO:49), TSSY (SEQ ID NO:50), VTAF (SEQ ID NO:51) and VSAF (SEQ ID NO:52). Representative nonclassical cadherin CAR sequences include the VE-cadherin CAR sequence DAE; the OB-cadherin CAR sequences DDK, EEY and EAQ; the dsg CAR sequences NQK, NRN and NKD and the dsc CAR sequences EKD and ERD.

A linker may be any molecule (including peptide and/or non-peptide sequences as well as single amino acids or other molecules), that does not contain a CAR sequence and that can be covalently linked to at least two peptide sequences. Using a linker, LYHY (SEQ ID NO:1)-containing peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, LYHY (SEQ ID NO:1) and HAV. Within another embodiment, modulating agents having a branched structure may comprise, for example, LYHY (SEQ ID NO:1), along with one or more of a claudin CAR sequence; a VE-cadherin CAR sequence; a dsg CAR sequence and/or a dsc CAR sequence. Linkers preferably produce a distance between CAR sequences between 0.1 to 10,000 nm, more preferably about 0.1–400 nm. A separation distance between recognition sites may generally be determined according to the desired function of the modulating agent. For inhibitors of cell adhesion, the linker distance should be small (0.1–400 nm). For enhancers of cell adhesion, the linker distance should be 400–10,000 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

The total number of CAR sequences (including occludin CAR sequence(s), with or without other CAR sequences derived from one or more adhesion molecules) present within a modulating agent may range from 1 to a large number, such as 100, preferably from 1 to 10, and more preferably from 1 to 5. Peptide modulating agents comprising multiple CAR sequences typically contain from 4 to about 1000 amino acid residues, preferably from 4 to 50 residues. When non-peptide linkers are employed, each CAR sequence of the modulating agent is present within a peptide that generally ranges in size from 4 to 50 residues in length, preferably from 4 to 25 residues, more preferably from 4 to 16 residues and still more preferably from 4 to 15 residues. Additional residue(s) that may be present on the N-terminal and/or C-terminal side of a CAR sequence may be derived from sequences that flank the LYHY sequence within naturally occurring occludins with or without amino acid substitutions and/or other modifications. Flanking sequences for mammalian occludins are shown in FIG. 2, and in SEQ ID NOs:5–8. Alternatively, additional residues present on one or both sides of the CAR sequence(s) may be unrelated to an endogenous sequence (e.g., residues that facilitate purification or other manipulation and/or residues having a targeting or other function).

A modulating agent may contain sequences that flank the occludin CAR sequence on one or both sides, to enhance potency or specificity. A suitable flanking sequence for enhancing potency includes, but is not limited to, an endogenous sequence present in an occludin (shown in, for example, FIG. 2).

To facilitate the preparation of modulating agents having a desired potency, nuclear magnetic resonance (NMR) and computational techniques may be used to determine the conformation of a peptide that confers a known potency. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space. This information may be used to facilitate calculation of the lowest energy conformation for the LYHY (SEQ ID NO:1) sequence. Conformation may then be correlated with tissue specificity to permit the identification of peptides that are similarly tissue specific or have enhanced tissue specificity.

Modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule, α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol.

TABLE I

| Amino acid one-letter and three-letter abbreviations | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Certain preferred modulating agents for use within the present invention comprise at least one of the following sequences: QYLYHYCVVD (SEQ ID NO:2), YLYHYCVVD (SEQ ID NO:12), LYHYCVVD (SEQ ID NO:13), QYLYHYC (SEQ ID NO 14), YLYHYC (SEQ ID NO:15), LYHYC (SEQ ID NO:16), QYLYHY (SEQ ID NO:17), YLYHY (SEQ ID NO:18), and/or LYHY (SEQ ID NO:1), wherein each amino acid residue may, but need not, be modified as described above. Within other embodiments, a modulating agent may comprise a cyclic peptide of one of the following sequences: CLYHYC (SEQ ID NO:3), CYLYHYC (SEQ ID NO:40), CQYLYHYC (SEQ ID NO:41), KQYLYHYD (SEQ ID NO:42), YLYHY (SEQ ID NO:43), QYLYHY (SEQ ID NO:44) or KLYHYD (SEQ ID NO:45). Modulating agents comprising derivatives of any of the sequences recited herein (i.e., sequences having one or more C-terminal N-terminal and/or side chain modifications) are also encompassed by the present invention.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using standard solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the a-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

N-acetylation of the N-terminal residue can be accomplished by reacting the final peptide with acetic anhydride before cleavage from the resin. C-amidation may be accomplished using an appropriate resin such as methylbenzhydrylamine resin using the Boc technology.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous occludin or other adhesion molecule. Such sequences may be prepared based on known cDNA or genomic sequences (see Blaschuk et al., *J. Mol. Biol.* 211:679–682, 1990), or from sequences isolated by screening an appropriate library with probes designed based on known occludin sequences. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous occludin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, a modulating agent may comprise one or more cyclic peptides. Such cyclic peptides may contain only one CAR sequence, or may additionally contain one or more other adhesion molecule binding sites, which may or may not be CARs. Such additional sequences may be separated by a linker (i.e., one or more peptides not derived from a CAR sequence or other adhesion molecule binding site, as described previously). Within one such embodiment, a modulating agent comprises a cyclic peptide containing two LYHY (SEQ ID NO:1) sequences. Within another embodiment, a cyclic peptide contains one LYHY (SEQ ID NO:1) and one CAR sequence recognized by a different CAM. In certain preferred embodiments, the second CAR sequence is derived from fibronectin (i.e., RGD); a classical cadherin (i.e., HAV); a claudin or a nonclassical cadherin as described above.

Cyclic peptides containing at least one occludin CAR sequence may be covalently linked to either cyclic or linear peptides containing at least one CAR sequence recognized by a different CAM, as described previously. Using a linker, cyclic LYHY-containing peptides and other cyclic or linear peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise multiple different CAR sequences, such as various combinations of LYHY (SEQ ID NO:1), RGD, HAV, claudin CAR sequence(s) and/or nonclassical cadherin CAR sequence(s).

In addition to the CAR sequence(s), cyclic peptides generally comprise at least one additional residue, such that the size of the cyclic peptide ring ranges from 5 to about 15 residues, preferably from 5 to 10 residues. Such additional residue(s) may be present on the N-terminal and/or C-terminal side of a CAR sequence, and may be derived from sequences that flank the endogenous occludin CAR sequence with or without amino acid substitutions and/or other modifications. Alternatively, additional residues present on one or both sides of the CAR sequence(s) may be unrelated to an endogenous sequence (e.g., residues that facilitate cyclization).

Within certain preferred embodiments, as discussed below, relatively small cyclic peptides that do not contain significant sequences flanking the LYHY sequence are preferred for modulating occludin mediated cell adhesion. Such peptides may contain an N-acetyl group and a C-amide group (e.g., the 6-residue ring N-Ac-<u>CLYHYC</u>-NH$_2$ (SEQ ID NO:3). Within the context of the present invention, underlined peptide sequences indicate cyclic peptides, wherein the cyclization is performed by any suitable method as provided herein.

Within other preferred embodiments, a cyclic peptide may contain sequences that flank the LYHY (SEQ ID NO:1) sequence in a native occludin molecule on one or both sides. Such sequences may result in increased potency. Suitable flanking sequences include, but are not limited to, the endogenous sequence present in naturally occurring occludin. To facilitate the preparation of cyclic peptides having increased potency, nuclear magnetic resonance (NMR) and computational techniques may be used to determine the conformation of a peptide that confers increased potency, as described above.

Cyclic peptides as described herein may comprise residues of L-amino acids, D-amino acids, or any combination thereof. A cyclic peptide may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Cyclic peptides as described herein may be synthesized by methods well known in the art, including recombinant DNA methods and chemical synthesis. Following synthesis of a linear peptide (utilizing methods described herein), with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing H$_2$O as a side product. Alternatively, strong oxidizing agents such as I$_2$ and K$_3$Fe(CN)$_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs: 19 and 20), in which the underlined portion is cyclized:

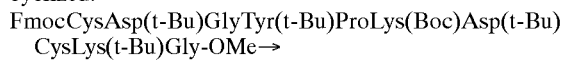

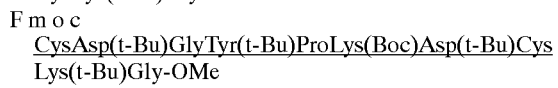

Oxidizing agents also allow concurrent deprotection/oxidation of suitable S-protected linear precursors to avoid premature, nonspecific oxidation of free cysteine, as shown below (SEQ ID Nos:21 and 22), where X and Y=S-Trt or S-Acm:

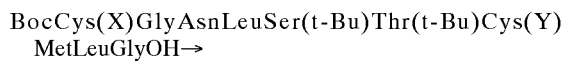

DMSO, unlike I$_2$ and K$_3$Fe(CN)$_6$, is a mild oxidizing agent which does not cause oxidative side reactions of the nucleophilic amino acids mentioned above. DMSO is miscible with H$_2$O at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs:23 and 24), X is Acm, Tacm or t-Bu:

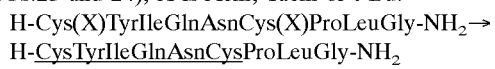

Suitable thiol-containing residues for use in such oxidation methods include, but are not limited to, cysteine. β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by —NH$_2$:

i) N-Ac-<u>Cys-Leu-Tyr-His-Tyr-Cys</u>-NH$_2$ (SEQ ID NO:25)
ii) H-<u>Cys-Leu-Tyr-His-Tyr-Cys</u>-OH (SEQ ID NO:26)
iii) N-Ac-<u>Cys-Gln-Tyr-Leu-Tyr-His-Tyr-Cys</u>-NH$_2$ (SEQ ID NO:27)
iv) H-<u>Cys-Gln-Tyr-Leu-Tyr-His-Tyr-Cys</u>-OH (SEQ ID NO:28)
v) N-Ac-<u>Cys-Tyr-Leu-Tyr-His-Tyr-Cys</u>-NH$_2$ (SEQ ID NO:29)

vi) H-Cys-Tyr-Leu-Tyr-His-Tyr-Cys-OH (SEQ ID NO:30)
vii) N-Ac-Cys-Leu-Tyr-His-Tyr-Pen-NH$_2$ (SEQ ID NO:31)
viii) N-Ac-Tmc-Leu-Tyr-His-Tyr-Cys-NH$_2$ (SEQ ID NO:32)
ix) N-Ac-Pmc-Leu-Tyr-His-Tyr-Cys-NH$_2$ (SEQ ID NO:33)
x) N-Ac-Mpr-Leu-Tyr-His-Tyr-Cys-NH$_2$ (SEQ ID NO:34)
xi) N-Ac-Pmp-Leu-Tyr-His-Tyr-Cys-NH$_2$ (SEQ ID NO:35)

xii)

xiii)

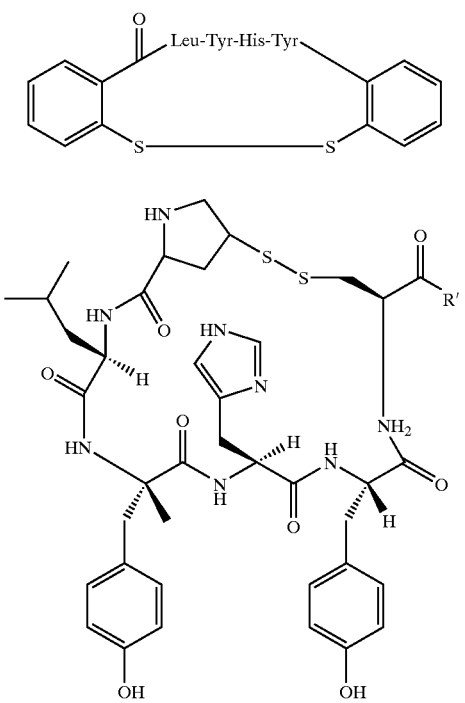

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are YLYHY (SEQ ID NO.18) and QYLYHY (SEQ ID NO:17). Within another such embodiment, the cyclic peptide comprises a D-amino acid (e.g., yLYHY; SEQ ID NO:18). Alternatively, cyclization may be accomplished by linking one terminus and a residue side chain or using two side chains, as in KLYHYD (SEQ ID NO:36) or KQYLYHYD (SEQ ID NO:37), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

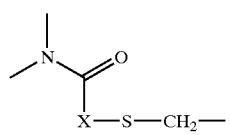

ii.

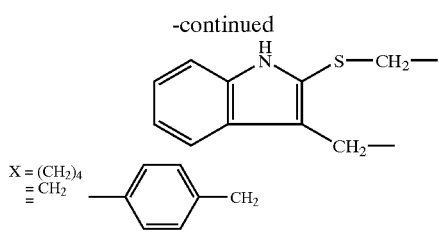

Cyclization may also be achieved using $\delta_1,\delta_1$-Ditryptophan (i.e., Ac-Trp-Gly-Gly-Trp-OMe) (SEQ ID NO:38), as shown below:

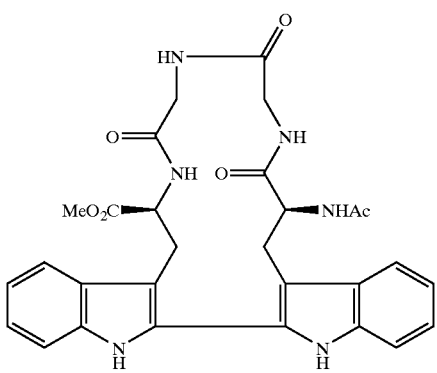

Representative structures of cyclic peptides are provided in FIG. 3. Within FIG. 3, certain cyclic peptides having the ability to modulate cell adhesion (shown on the left) are paired with similar inactive structures (on the right). The structures and formulas recited herein are provided solely for the purpose of illustration, and are not intended to limit the scope of the cyclic peptides described herein.

As noted above, instead of (or in addition to) an occludin CAR sequence, a modulating agent may comprise an antibody, or antigen-binding fragment thereof, that specifically binds to a occludin CAR sequence. As used herein, an antibody, or antigen-binding fragment thereof, is said to "specifically bind" to a occludin CAR sequence (with or without flanking amino acids) if it reacts at a detectable level with a peptide containing that sequence, and does not react detectably with peptides containing a different CAR sequence or a sequence in which the order of amino acid residues in the occludin CAR sequence and/or flanking sequence is altered. Such antibody binding properties may be assessed using an ELISA, as described by Newton et al., *Develop. Dynamics* 197:1–13, 1993.

Polyclonal and monoclonal antibodies may be raised against an occludin CAR sequence using conventional techniques. See, e.g., Harlow and Lane, *Antibodies: A Laboratory Manual*, Cold Spring Harbor Laboratory, 1988. In one such technique, an immunogen comprising the occludin CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the occludin CAR sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target occludin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988, see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, modulating agents as described herein are capable of modulating occludin-mediated cell adhesion. The ability of an agent to modulate cell adhesion may generally be evaluated in vitro by assaying the effect on endothelial and/or epithelial cell adhesion using, for example, any of a variety of immunostaining protocols and/or plating assays. In general, a modulating agent is an inhibitor of cell adhesion if contact of the test cells with the modulating agent results in a discernible disruption of cell adhesion using one or more representative assays provided herein. Modulating agents that enhance cell adhesion (e.g., agents comprising multiple LYHY (SEQ ID NO:1) sequences and/or linked to a support molecule or material) are considered to be modulators of cell adhesion if they are capable of promoting cell adhesion, as judged by plating assays to assess either endothelial or epithelial cell adhesion to a modulating agent attached to a support material, such as tissue culture plastic.

The ability of an agent to modulate cell adhesion may generally be evaluated in vivo by assessing the effect on vascular permeability utilizing the Miles assay (McClure et al., *J. Pharmacological & Toxicological Methods* 32:49–52, 1994). Briefly, a candidate modulating agent may be dissolved in phosphate buffered saline (PBS) at a concentration of 100 μg/ml. Adult rats may be given 100 μl subdermal injections of each peptide solution into their shaved backs, followed 15 minutes later by a single 250 μl injection of 1% Evans blue dissolved in PBS into their tail veins. The subdermal injection sites may be visually monitored for the appearance of blue dye. Once the dye appears (about 15 minutes after injection), each subdermal injection site may be excised, weighed, and placed in 1 ml dimethylformamide for 24 hours to extract the dye. The optical density of the dye extracts may then be determined at 620 nm. In general, the injection of 0.1 ml of modulating agent (at a concentration of 0.1 mg/ml) into the backs of rats causes an increase of dye accumulation at the injection sites of at least 50%, as compared to dye accumulation at sites into which PBS has been injected.

The effect of a modulating agent on endothelial cell adhesion may generally be evaluated using immunolocalization techniques. Human aortic endothelial cells (HAEC) may be cultured on fibronectin-coated coverslips (fibronectin may be obtained from Sigma, St. Louis, Mo.) according to the procedures of Jaffe et al., *J. Clin. Invest.* 52:2745–2756, 1973. Briefly, human endothelial cells may be maintained in EGM (endothelial cell growth medium; Clonetics, San Diego, Calif.) and used for experiments at passage 4. Confluent cultures of HAEC may be exposed to either a candidate modulating agent (final concentration 100 µg/ml EGM), or EGM alone for 1 hour. The cells are then be fixed for 30 minutes at 4° C. in 95% ethanol, followed by fixation in acetone for 1 minute at 4° C. (Furuse et al.,*J. Cell Biol.* 123:1777–1788, 1993). After fixation, the cells may be probed with either mouse anti-VE-cadherin antibodies (Hemeris, Sassenage, France; diluted 1:250 in 0.1% dried skim milk powder dissolved in PBS), or rabbit anti-occludin antibodies (Zymed, South San Francisco, Calif.; diluted 1:300 in 0.1% dried skim milk powder dissolved in PBS) for 1 hour at 37° C. The cells may then be washed with 0.1% dried skim milk powder dissolved in PBS (three washes, 5 minutes/wash), and probed with secondary antibodies (donkey anti-mouse Cy3, or donkey anti-rabbit Cy5 diluted 1:250 in 0.1% dried skim milk powder dissolved in PBS; Jackson Immunoresearch Laboratories Inc., Westgrove, Pa.) for 1 hour at 37° C. The cells may then be washed again with in 0.1% dried skim milk powder dissolved in PBS and mounted in a solution composed of 50% glycerol and 50% PBS to which phenylenediamine (Sigma, St. Louis, Mo.) has been added to a final concentration of 1 mg/ml. The sample may then be analyzed using a Bio-Rad MRC 1000 confocal microscope with Laser Sharp software version 2.1T (Bio-Rad, Hercules, Calif.). In general, 0.1 mg/ml of modulating agent results in the appearance of intercellular gaps within the monolayer cultures and a decrease of at least 50% in the surface expression of occludin and VE-cadherin, as compared to monolayer cultures that were not exposed to the modulating agent.

Within certain cell adhesion assays, the addition of a modulating agent to cells that express occludin results in disruption of cell adhesion. An "occludin-expressing cell," as used herein, may be any type of cell that expresses occludin on the cell surface at a detectable level, using standard techniques such as immunocytochemical protocols (e.g., Blaschuk and Farookhi, *Dev. Biol.* 136:564–567, 1989). Occludin-expressing cells include endothelial, epithelial and/or cancer cells. For example, such cells may be plated under standard conditions that, in the absence of modulating agent, permit cell adhesion. In the presence of modulating agent (e.g., 100 µg/mL), disruption of cell adhesion may be determined visually within 24 hours, by observing retraction of the cells from one another.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J. Cell Biol.* 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 0.1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of rabbit anti-occludin antibody ((Zymed, South San Francisco, Calif.) and mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse Cy3 and donkey anti-rabbit Cy5 (Jackson Immunoresearch Laboratories Inc., Westgrove, Pa.) for 1 hour at 37° C. Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts occludin-mediated cell adhesion may assume a non-polygonal and elongated morphology (i.e., a fibroblast-like shape) within 48 hours of treatment with 0.1 mg/mL of modulating agent. Gaps appear in confluent cultures of such cells. In addition, 0.1 mg/mL of such a modulating agent reproducibly induces a readily apparent reduction in cell surface staining of occludin and E-cadherin, as judged by immunofluorescence microscopy (Laird et al., *J. Cell Biol.* 131:1193–1203, 1995), of at least 75% within 48 hours.

A third cell adhesion assay involves evaluating the effect of a modulating agent on permeability of adherent endothelial cell monolayers. The effects of a modulating agent on the permeability of endothelial cell monolayers may be assessed utilizing the protocols of Ehringer et al., *J. Cell. Physiol.* 167:562–569, 1996. HAEC can be seeded onto inserts in 24-well plates (Becton-Dickenson, Franklin Lake, N.J.) and cultured in EGM. Confluent cell monolayers may be exposed to either modulating agent (final concentration 100 µg/ml EGM), or EGM alone for 1 hour. The inserts may then be transferred to 24-chamber plates (Becton-Dickenson) for permeability assays. Perfusate (0.5% bovine serum albumin, fraction V (Sigma) dissolved in 15 mM HEPES, pH 7.4) and FITC-Dextran (50 µg/ml HEPES buffer, MW 12 kDa; Sigma) may be added to each well (1 ml/well and 50 µl/well, respectively), and the cells incubated at 37° C. for 30 min. Aliquots of 100 µl may then be removed from the lower chamber and the optical density of the solution determined at a wavelength of 450 nm. In general, the presence of 100 µg/mL modulating agent that enhances the permeability of endothelial cell monolayers results in a statistically significant increase in the amount of marker in the receptor compartment after 1 hour.

Yet another assay evaluates the effect of an occludin modulating agent on the electrical resistance across a monolayer of cells. For example, Madin Darby canine kidney (MDCK) cells can be exposed to the modulating agent dissolved in medium (e.g., at a final concentration of 0.5 mg/ml for a period of 24 hours). The effect on electrical resistance can be measured using standard techniques. This assay evaluates the effect of a modulating agent on tight junction formation in epithelial cells. In general, the presence of 500 µg/mL modulating agent should result in a statistically significant increase or decrease in electrical resistance after 24 hours.

A further assay for evaluating modulating agent activity involves determining an effect of a candidate agent on neutrophil migration on endothelial cells. Within such assays, endothelial cells (e.g., HUVEC) may be harvested and cultured using standard techniques. Cells are grown to confluence on 8.0 μm pore cell culture inserts (Falcon, Franklin Lake, N.J.) essentially as described by Ohno et al., *Inflammation* 21(3):313–24, 1997. Radiolabeled human neutrophils (polymorphonuclear leukocytes, PMN) are added to the apical surface of HUVEC monolayers and allowed to migrate. Migration assays are generally performed in the presence of $10^{-7}$ M N-formyl-methionyl-leucyl-phenylalanine (fMLP), a chemoattractant that causes the leukocytes to undergo diapedesis. PMN migration may be quantitated as follows:

$$\% \text{ Migration} = \frac{\text{Lower chamber (cpm)}}{[\text{Upper chamber (cpm)} + \text{lower chamber (cpm)}]}$$

In general, the presence of 500 μg/mL modulating agent should result in a statistically significant increase or decrease in percent migration after 1 hour.

Within another assay, a candidate modulating agent may be evaluated for the ability to increase transendothelial permeability. Endothelial barrier function may be evaluated by measuring the transendothelial flux of FITC dextran using monolayers of human umbilical vein endothelial cells. To perform solute flux (permeability) measurements, monolayers may be incubated in the presence and absence of candidate modulating agent in peptide culture dishes, such that the monolayer divides the medium into two compartments. FITC-dextran (10 kD) may be added to one compartment, and incubated, after which the contents of the other compartment may be assayed spectrophotometrically. In general, the presence of 500 μg/mL modulating agent should result in a statistically significant increase in permeability after 1 hour.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than occludin. Such modulators may generally be prepared as described above, incorporating one or more non-occludin CAR sequences and/or antibodies thereto in place of the occludin CAR sequence and antibodies. Such compositions are particularly useful for situations in which it is desirable to inhibit cell adhesion mediated by multiple cell adhesion molecules, such as cadherins (e.g., classical cadherins, E-cadherin, Dsg and Dsc); integrins; members of the immunoglobulin supergene family (such as N-CAM and PECAM); and claudins. Preferred CAR sequences for use within such a modulator include HAV, RGD, and CAR sequences of claudins, VE-cadherin, dsg and dsc.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented) Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably from 0.0001% to 0.2% and more preferably from 0.01% to 0.1%. Fluid compositions typically contain an amount of modulating agent ranging from 10 ng/ml to 5 mg/ml, preferably from 10 $\mu$g to 2 mg/mL. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of occludin-expressing cells in vitro and/or in vivo. As noted above, modulating agents for purposes that involve the disruption of occludin-mediated cell adhesion may comprise an occludin CAR sequence, multiple occludin CAR sequences in close proximity and/or an antibody (or an antigen-binding fragment thereof) that recognizes the occludin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the occludin CAR sequence by linkers. As noted above, such linkers may or may not comprise one or more amino acids. For enhancing cell adhesion, a modulating agent may contain multiple occludin CAR sequences or antibodies (or fragments), preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of occludin-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of a target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within certain aspects, the present invention provides methods in which cell adhesion is diminished. In one such aspect, methods for reducing unwanted cellular adhesion by administering a modulating agent are provided. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods include H-QYLYHYCVVD-OH (SEQ ID NO:2) and H-CLYHYC-OH (SEQ ID NO:3) and modulating agents comprising such sequences or derivatives thereof. Preferred antibody modulating agents include Fab fragments directed against either H-QYLYHYCVVD-OH (SEQ ID NO:2) or H-CLYHYC-OH (SEQ ID NO:3). In addition, a modulating agent may comprise one or more of a claudin CAR sequence, a CAR sequence for a nonclassical cadherin (such as VE-cadherin, OB-cadherin, dsc or dsg), RGD sequence, and/or HAV sequence separated from an occludin CAR sequence via a linker. Alternatively, separate modulators of cadherin- and integrin-mediated cell adhesion may be administered in conjunction with the modulating agent(s), either within the same pharmaceutical composition or separately. Topical administration of the modulating agent(s) is generally preferred, but other means may also be employed. Preferably, a fluid composition for topical administration (comprising, for example, physiological saline) comprises an amount of modulating agent as described above, and more preferably from 10 μg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within a further aspect, methods are provided for enhancing delivery of a drug to a tumor in a mammal, comprising administering a modulating agent in combination with a drug to a tumor-bearing mammal. Preferred modulating agents for use within such methods include H-QYLYHYCVVD-OH (SEQ ID NO:2) and H-CLYHYC-OH (SEQ ID NO:3) and modulating agents comprising such sequences or derivatives thereof. Preferred antibody modulating agents include Fab fragments directed against either H-QYLYHYCVVD-OH (SEQ ID NO:2) or H-CLYHYC-OH (SEQ ID NO:3). In one particularly preferred embodiment, a modulating agent is capable of disrupting cell adhesion mediated by multiple adhesion molecules. For example, a single branched modulating agent (or multiple agents linked to a single molecule or support material) may disrupt occludin, classical cadherin, integrin, and nonclassical cadherin (e.g., Dsc and Dsg) mediated cell adhesion, thereby disrupting tight junctions, adherens junctions, and desmosomes. Multifunctional modulating agents comprising an occludin CAR sequence linked to an RGD sequence and/or CAR sequencers) for one or more of a classical cadherin, claudin or nonclassical cadherin (e.g., OB-cadherin, VE-cadherin, dsc or dsg) may be used to disrupt cell adhesion. Alternatively, a separate modulator of non-occludin-mediated cell adhesion may be administered in conjunction with the modulating agent(s), either within the same pharmaceutical composition or separately. Preferred antibody modulating agents that may be used in conjunction with the occludin modulating agents include Fab fragments directed against either an N-cadherin CAR sequence (such as FHLRAHAVDINGNQV-$NH_2$; SEQ ID NO:4) or an E-cadherin CAR sequence LFSHAVSSNG-$NH_2$ (SEQ ID NO:39).

Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 µg/mL to about 2 mg/mL, and more preferably from about 10 µg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer and/or inhibiting metastasis.

Preferred modulating agents for use within such methods include H-QYLYHYCVVD-OH (SEQ ID NO:2) and H-CLYHYC-OH (SEQ ID NO:3) and modulating agents comprising such sequences or derivatives thereof. Preferred antibody modulating agents include Fab fragments directed against either H-QYLYHYCVVD-OH (SEQ ID NO:2) or H-CLYHYC-OH (SEQ ID NO:3). In one particularly preferred embodiment, a modulating agent is capable of disrupting cell adhesion mediated by multiple adhesion molecules. For example, a single branched modulating agent (or multiple agents linked to a single molecule or support material) may disrupt occludin, classical cadherin, integrin, Dsc and Dsg mediated cell adhesion, thereby disrupting tight junctions, adherens junctions, focal contacts and desmosomes. Multifunctional modulating agents comprising the occludin CAR sequence linked to one or more of a claudin CAR sequence, VE-cadherin CAR sequence, dsc CAR sequence, dsg CAR sequence, RGD sequence, OB-cadherin CAR sequence and/or HAV sequence may be used to disrupt cell adhesion. Alternatively, a separate modulator of non-occludin-mediated cell adhesion may be administered in conjunction with the modulating agent(s), either within the same pharmaceutical composition or separately. Preferred antibody modulating agents that may be used in conjunction with the occludin modulating agents include Fab fragments directed against either an N-cadherin CAR sequence, such as FHLRAHAVDINGNQV-NH$_2$ (SEQ ID NO:4), or an E-cadherin CAR sequence, such as LFSHAVSSNG-NH$_2$ (SEQ ID NO:39). A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

It has further been found, within the context of the present invention, that modulating agents provided herein may be used to increase immune cell (e.g., leukocyte) infiltration into tumors, resulting in cancer immunotherapy. Modulating agents may also be used to treat leukemias. Preferred modulating agents for use within such methods include H-QYLYHYCVVD-OH (SEQ ID NO:2) and H-CLYHYC-OH (SEQ ID NO:3) and modulating agents comprising such sequences or derivatives thereof. Preferred antibody modulating agents include Fab fragments directed against either H-QYLYHYCVVD-OH (SEQ ID NO:2) or H-CLYHYC-OH (SEQ ID NO:3). In one particularly preferred embodiment, a modulating agent is capable of disrupting cell adhesion mediated by multiple adhesion molecules. For example, a single branched modulating agent (or multiple agents linked to a single molecule or support material) may disrupt occludin, classical cadherin, integrin, Dsc and Dsg mediated cell adhesion, thereby disrupting tight junctions, adherens junctions, focal contacts and desmosomes. Multifunctional modulating agents comprising the occludin CAR sequence linked to one or more of a claudin CAR sequence, VE-cadherin CAR sequence, dsc CAR sequence, dsg CAR sequence, RGD sequence, OB-cadherin CAR sequence and/or HAV sequence may be used to disrupt cell adhesion. Alternatively, a separate modulator of non-occludin-mediated cell adhesion may be administered in conjunction with the modulating agent(s), either within the same pharmaceutical composition or separately. Preferred antibody modulating agents that may be used in conjunction with the occludin modulating agents include Fab fragments directed against either an N-cadherin CAR sequence, such as FHLRAHAVDINGNQV-NH$_2$ (SEQ ID NO:4), or an E-cadherin CAR sequence, such as LFSHAVSSNG-NH$_2$ (SEQ ID NO:39). A modulating agent may be administered alone (e.g., via the skin) or within a pharmaceutical composition. For melanomas and certain other accessible tumors, injection or topical administration as described above may be preferred. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above.

Within a further related aspect, a modulating agent may be used to inhibit angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for use within such methods include H-QYLYHYCVVD-OH (SEQ ID NO:2) and H-CLYHYC-OH (SEQ ID NO:3) and modulating agents comprising such sequences or derivatives thereof. Preferred antibody modulating agents include Fab fragments directed against either H-QYLYHYCVVD-OH (SEQ ID NO:2) or H-CLYHYC-OH (SEQ ID NO:3). In one particularly preferred embodiment, a modulating agent is capable of disrupting cell adhesion mediated by multiple adhesion molecules. For example, a single branched modulating agent (or multiple agents linked to a single molecule or support material) may disrupt occludin, classical cadherin, and integrin mediated cell adhesion, thereby disrupting tight junctions, adherens junctions, and focal contacts. Multifunctional modulating agents comprising the occludin CAR sequence linked to one or more of a claudin CAR sequence, VE-cadherin CAR sequence, dsc CAR sequence, dsg CAR sequence, RGD sequence, and/or HAV sequence may be used to disrupt cell adhesion. Alternatively, a separate modulator of non-occludin-mediated cell adhesion may be administered in conjunction with the modulating agent(s), either within the same pharmaceutical composition or separately. Preferred antibody modulating agents that may be used in conjunction with the occludin modulating agents include Fab fragments directed against an N-cadherin CAR sequence, such as FHLRAHAVDINGNQV-NH$_2$ (SEQ ID NO:4).

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 5 to 50 µg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 50 µg/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in an occludin-expressing cell. In general, patients afflicted with cancer may benefit from such treatment. Preferred modulating agents for use within such methods include H-QYLYHYCVVD-OH (SEQ ID NO:2) and H-CLYHYC-OH (SEQ ID NO:3) and modulating agents comprising such sequences or derivatives thereof. Preferred antibody modulating agents include Fab fragments directed against either H-QYLYHYCVVD-OH (SEQ ID NO:2) or H-CLYHYC-OH (SEQ ID NO:3). In one particularly preferred embodiment, a modulating agent is capable of disrupting cell adhesion mediated by multiple adhesion molecules. For example, a single branched modulating agent (or multiple agents linked to a single molecule or support material) may disrupt occludin, classical cadherin, and integrin mediated cell adhesion, thereby disrupting tight junctions, adherens junctions, and focal contacts. Multifunctional modulating agents comprising the occludin CAR sequence linked to one or more of a claudin CAR sequence, nonclassical cadherin CAR sequence (e.g., VE-cadherin, OB-cadherin, dsc or dsg), RGD sequence, and/or HAV sequence may be used to disrupt cell adhesion. Alternatively, a separate modulator of non-occludin-mediated cell adhesion may be administered in conjunction with the modulating agent(s), either within the same pharmaceutical composition or separately. Preferred antibody modulating agents that may be used in conjunction with the occludin modulating agents include Fab fragments directed against either an N-cadherin CAR sequence, such as FHLRAHAVDINGNQV-NH$_2$ (SEQ ID NO:4), or an E-cadherin CAR sequence, such as LFSHAVSSNG-NH$_2$ (SEQ ID NO:39).

Administration of modulating agents to induce apoptosis may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The following Examples are offered by way of illustration and not by way of limitation.

EXAMPLE 1

Preparation of Representative Cyclic Peptides

This Example illustrates the solid phase synthesis of representative linear and cyclic peptides as modulating agents.

The peptides were assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the α-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

EXAMPLE 2

Establishment of a Model System for Assessing Endothelial Cell Adhesion

This Example illustrates an endothelial cell adhesion assay for evaluating the effects of occludin-modulating agents on endothelial cell adhesion.

A. Cell Culture

Human aortic endothelial cells (HAEC) were cultured on fibronectin (Sigma, St. Louis, Mo.) according to the procedures of Jaffe et al., *J. Clin. Invest.* 52:2745–2756, 1973. Cells were maintained in EGM (endothelial cell growth medium; Clonetics, San Diego, Calif.) and used for experiments at passage 4.

B. Occludin and VE-cadherin Immunolocalization Methods

Figure 4B:
FIGS. 4A and 4B are immunofluorescence photographs of monolayer cultures of human aortic endothelial cells immunolabeled for occludin (red color) and VE-cadherin (green color). Colocalization of occludin and VE-cadherin is indicated by the yellow color. Arrows indicate gaps between the cells. The cells were either not treated (FIG. 4A), or exposed for 1 hour to 100 µg/ml H-QYLYHYCVVD-OH (Peptide 3; SEQ ID NO:2.
Figure 4A:
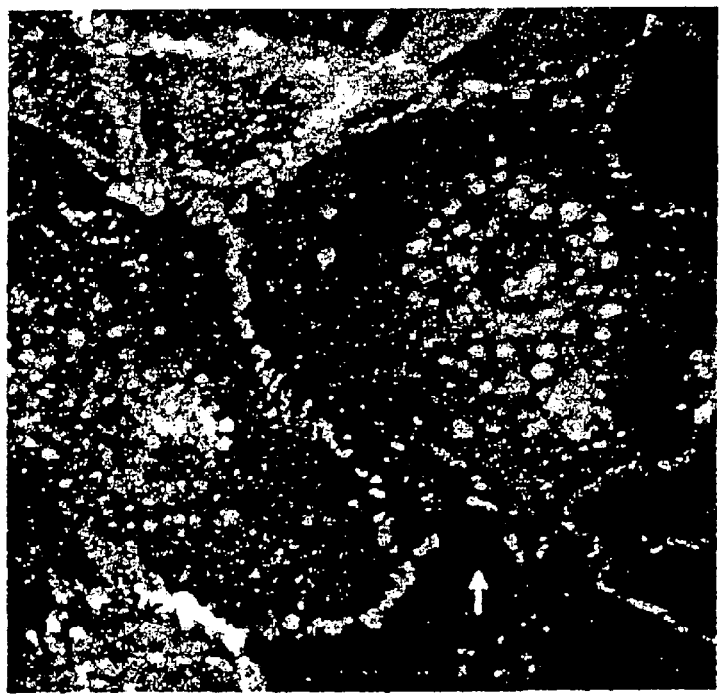

HAEC were cultured on fibronectin-coated coverslips. Confluent cultures of HAEC were exposed to linear peptides (final concentration 100 µg/ml EGM), or EGM alone for 1 hour. The cells were then fixed for 30 minutes at 4° C. in 95% ethanol, followed by fixation in acetone for 1 minute at 4° C. (Furuse et al., *J. Cell Biol.* 123:1777–1788, 1993). After fixation, the cells were allowed to air dry at room temperature. The cells were probed with either mouse anti-VE-cadherin antibodies (Hemeris, Sassenage, France; diluted 1:250 in 0.1% dried skim milk powder dissolved in PBS), or rabbit anti-occludin antibodies (Zymed, South San Francisco, Calif.; diluted 1:300 in 0.1% dried skim milk powder dissolved in PBS) for 1 hour at 37° C. The cells were then washed with 0.1% dried skim milk powder dissolved in PBS (three washes, 5 minutes/wash), and probed with secondary antibodies (donkey anti-mouse Cy3, or donkey anti-rabbit Cy5 diluted 1:250 in 0.1% dried skim milk powder dissolved in PBS; Jackson Immunoresearch Laboratories Inc., Westgrove, Pa.) for 1 hour at 37° C. The cells were washed again with in 0.1% dried skim milk powder dissolved in PBS and mounted in a solution composed of 50% glycerol and 50% PBS to which phenylenediamine (Sigma, St. Louis, Mo.) had been added to a final concentration of 1 mg/ml. The samples were analyzed using a Bio-Rad MRC 1000 confocal microscope with Laser Sharp software version 2.1T (Bio-Rad, Hercules, Calif.). Staining for occludin was assigned the pseudo-color red, whereas VE-cadherin staining was assigned pseudo-color green using Confocal Assistant 4.02 software. Immunofluorescence photographs of monolayer cultures of human aortic endothelial cells immunolabeled for occludin (red color) and VE-cadherin (green color) are shown in FIGS. 4A and 4B. Colocalization of occludin and VE-cadherin is indicated by the yellow color. Arrows indicate gaps between the cells. Note that the endothelial cells retract from one another when cultured in the presence of H-QYLYHYCVVD-OH (SEQ ID NO:2; FIG. 4B), indicating that adhesion is decreased between the cells. Furthermore, the cells do not form cobblestone-like monolayers when exposed to this peptide. Also note that surface expression of both VE-cadherin and occludin is greatly reduced in the cells treated with H-QYLYHYCVVD-OH (SEQ ID NO:2), as compared to the VE-cadherin and occludin levels expressed by untreated cells.

EXAMPLE 3

Effect of Representative Modulating Agents on Vasopermeability

This Example illustrates a vasopermeability assay for evaluating the effects of occludin-modulating agents on endothelial cell permeability in vivo.

A. Miles Assay for Vascular Permeability

Figure 5:
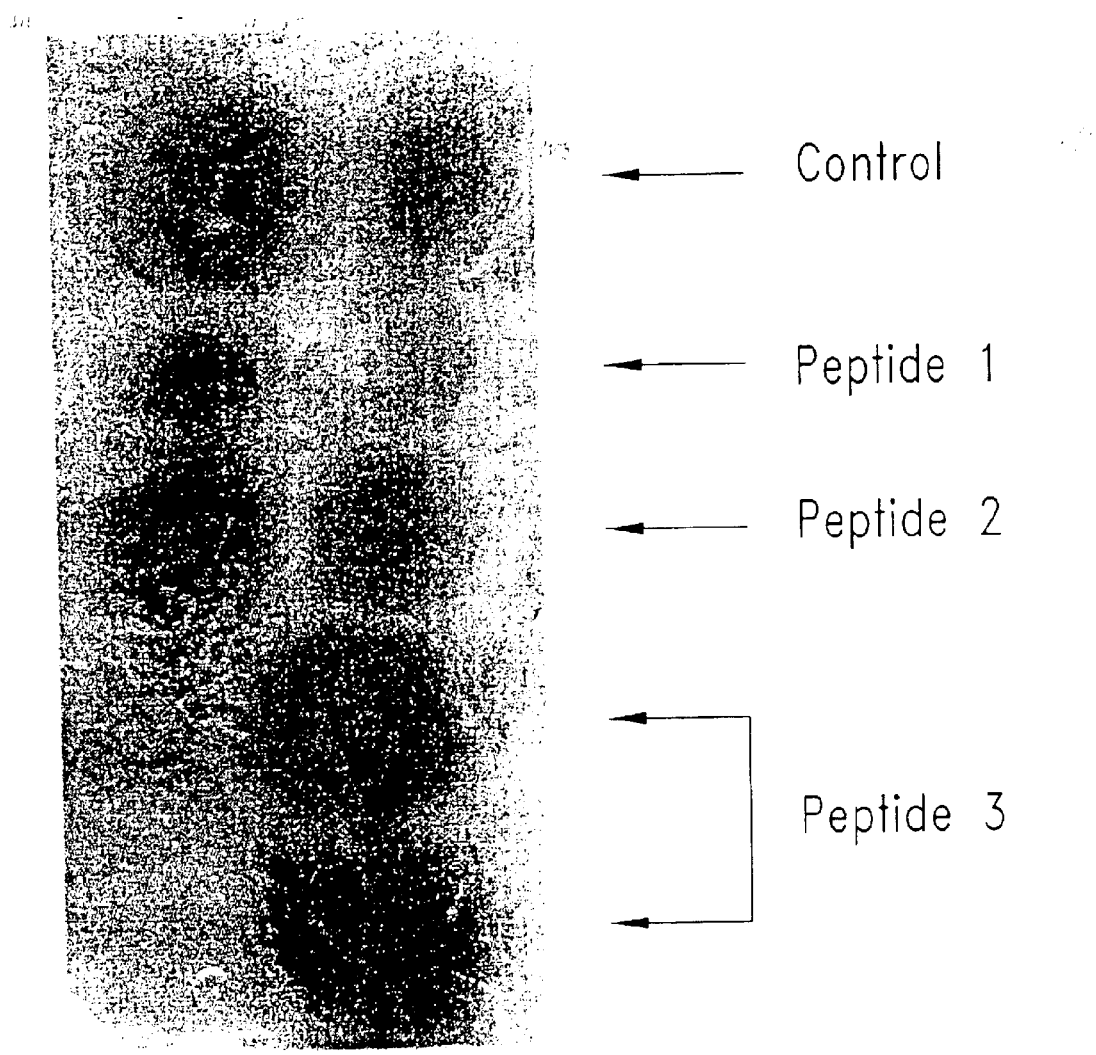
FIG. 5 is a photograph of the shaved back of a rat that received duplicate subdermal injections of either phosphate buffered saline, phosphate buffered saline containing acetyl-QYLYHYCVVD-NH$_2$ (SEQ ID NO:2; Peptide 1) H-QYLYHYCVVD-NH$_2$ (SEQ ID NO:2; Peptide 2), or H-QYLYHYCVVD-OH (SEQ ID NO:2; Peptide 3) at a concentration of 100 µg/ml, followed 15 minutes later by a single injection of Evans blue into the tail vein. The photograph was taken 15 minutes after injection of the dye.

The ability of cyclic and linear peptides to increase vascular permeability was assessed utilizing the Miles assay (McClure et al., *J. Pharmacological & Toxicological Meth.* 32:49–521994). The peptides were dissolved in phosphate buffered saline (PBS) at a concentration of 100 µg/ml. Adult rats were given 100 µl subdermal injections of each peptide solution into their shaved backs, followed 15 minutes later by a single 250 µl injection of 1% Evans blue dissolved in PBS into their tail veins. The subdermal injection sites were visually monitored for the appearance of blue dye. Once the dye appeared (15 minutes after injection), each subdermal injection site was excised, weighed, and placed in 1 ml dimethylformamide for 24 hours to extract the dye. The optical density of the dye extracts was determined at 620 nm. The effects of injecting either phosphate buffered saline, phosphate buffered saline containing acetyl-QYLYHYCVVD-NH$_2$ (SEQ ID NO:2) H-QYLYHYCVVD-NH$_2$ (SEQ ID NO:2), or H-QYLYHYCVVD-OH (SEQ ID NO:2) into sites along the shaved back of a rat on the accumulation of Evans blue at the injection sites is shown in FIG. 5. Note that more blue dye has accumulated at the sites where the peptide H-QYLYHYCVVD-OH (SEQ ID NO:2) was injected, as opposed to the sites where either phosphate buffered saline, phosphate buffered saline containing acetyl-QYLYHYCVVD-NH$_2$ (SEQ ID NO:2), or H-QYLYHYCVVD-NH$_2$ (SEQ ID NO:2) were injected.

Figure 6:
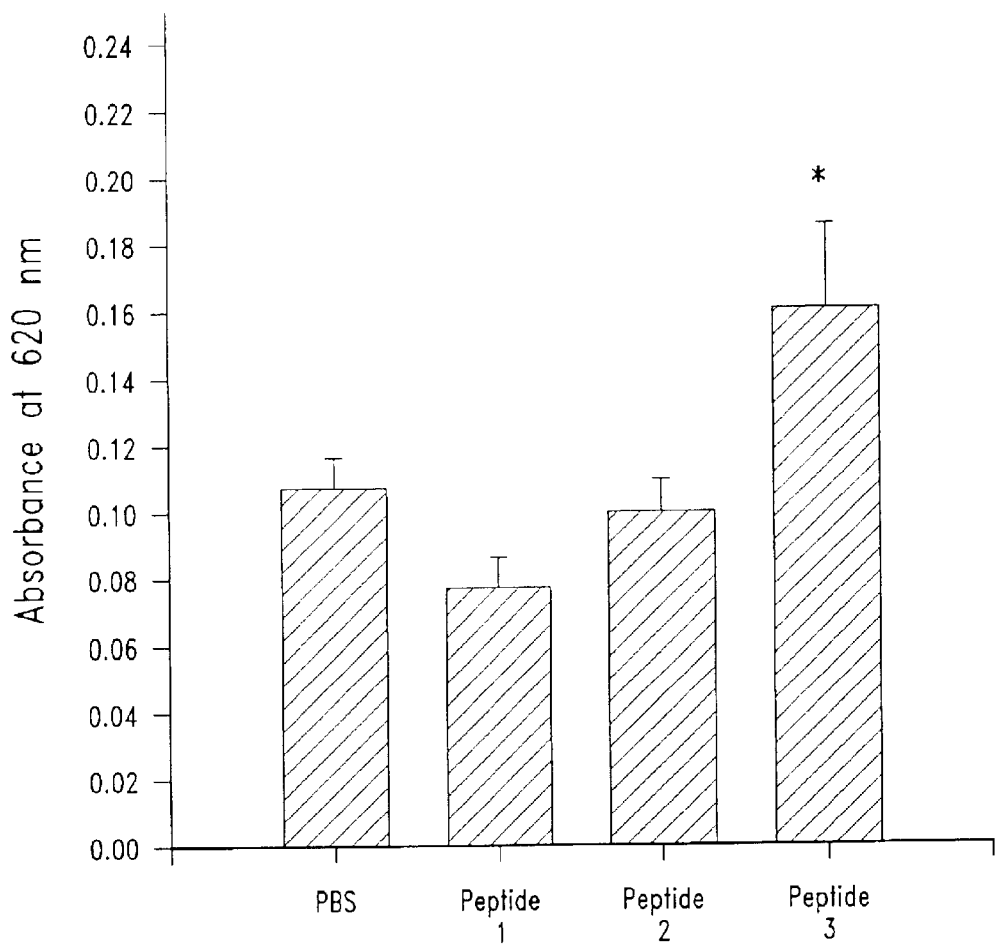
FIG. 6 is a histogram depicting the optical densities of dimethylformamide extracts prepared from the excised injection sites shown in FIG. 5, and showing that more dye was extracted from the sites injected with H-QYLYHYCVVD-OH (SEQ ID NO:2; Peptide 3), than from sites injected with either phosphate buffered saline, acetyl-QYLYHYCVVD-NH$_2$ (SEQ ID NO:2; Peptide 1) or H-QYLYLYCVVD-NH$_2$ (SEQ ID NO:2; Peptide 2).

FIG. 6 shows a histogram depicting the optical densities of dimethylformamide extracts prepared from the excised injection sites shown in FIG. 5. Note that more dye was extracted from the sites injected with H-QYLYHYCVVD-OH (SEQ ID NO:2), than from sites injected with either phosphate buffered saline, acetyl-QYLYHYCVVD-NH$_2$ (SEQ ID NO:2), or H-QYLYHYCVVD-NH$_2$ (SEQ ID NO:2).

Figure 7:
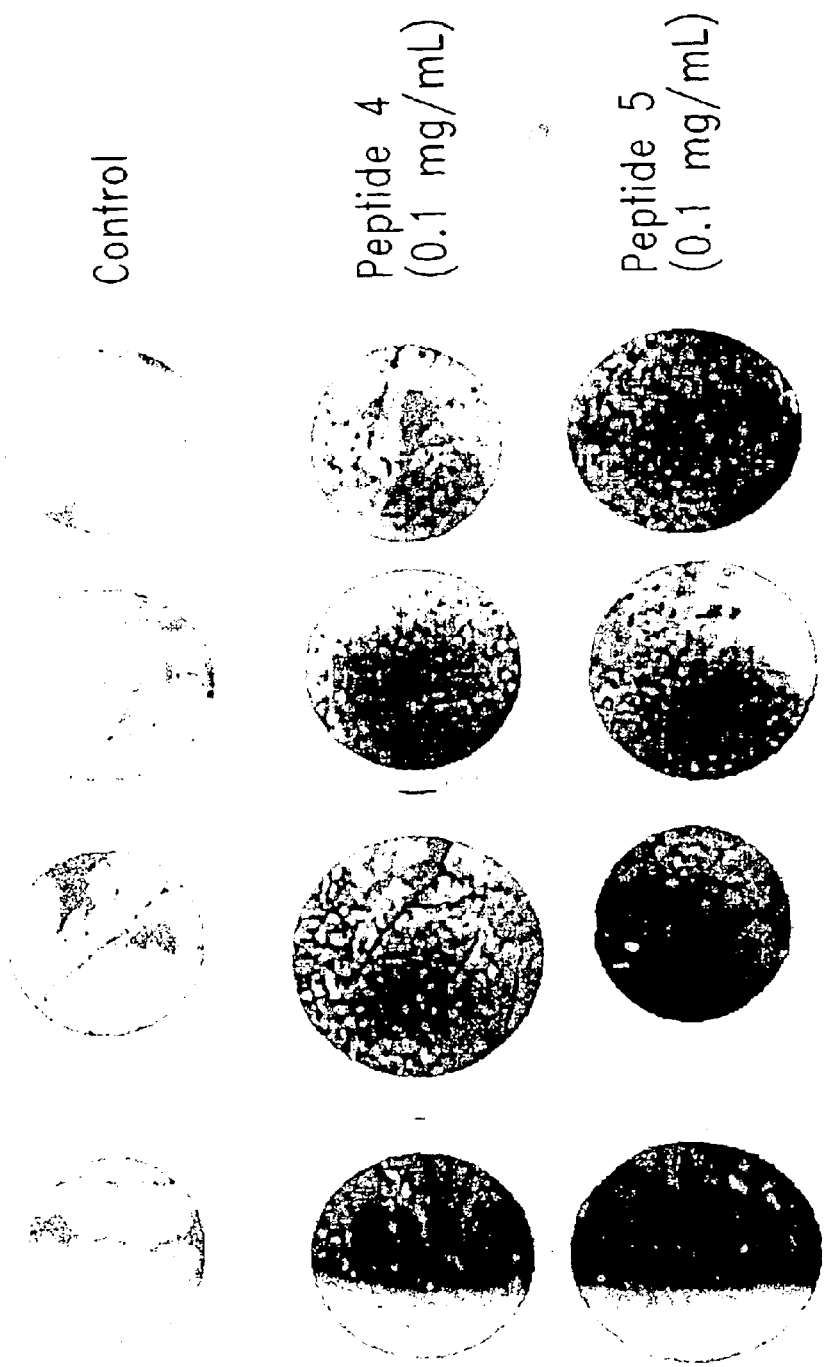
FIG. 7 is a series of photographs of the shaved back of a rat that received duplicate subdermal injections of either phosphate buffered saline, phosphate buffered saline containing acetyl-<u>CLYHYC</u>-NH$_2$ (SEQ ID NO:3; Peptide 4), or H-<u>CLYHYC</u>-OH (SEQ ID NO:3; Peptide 5) at a concentration of 100 µg/ml, followed 15 minutes later by a single injection of Evans blue into the tail vein. The photographs were taken 15 minutes after injection of the dye.
Figure 8:
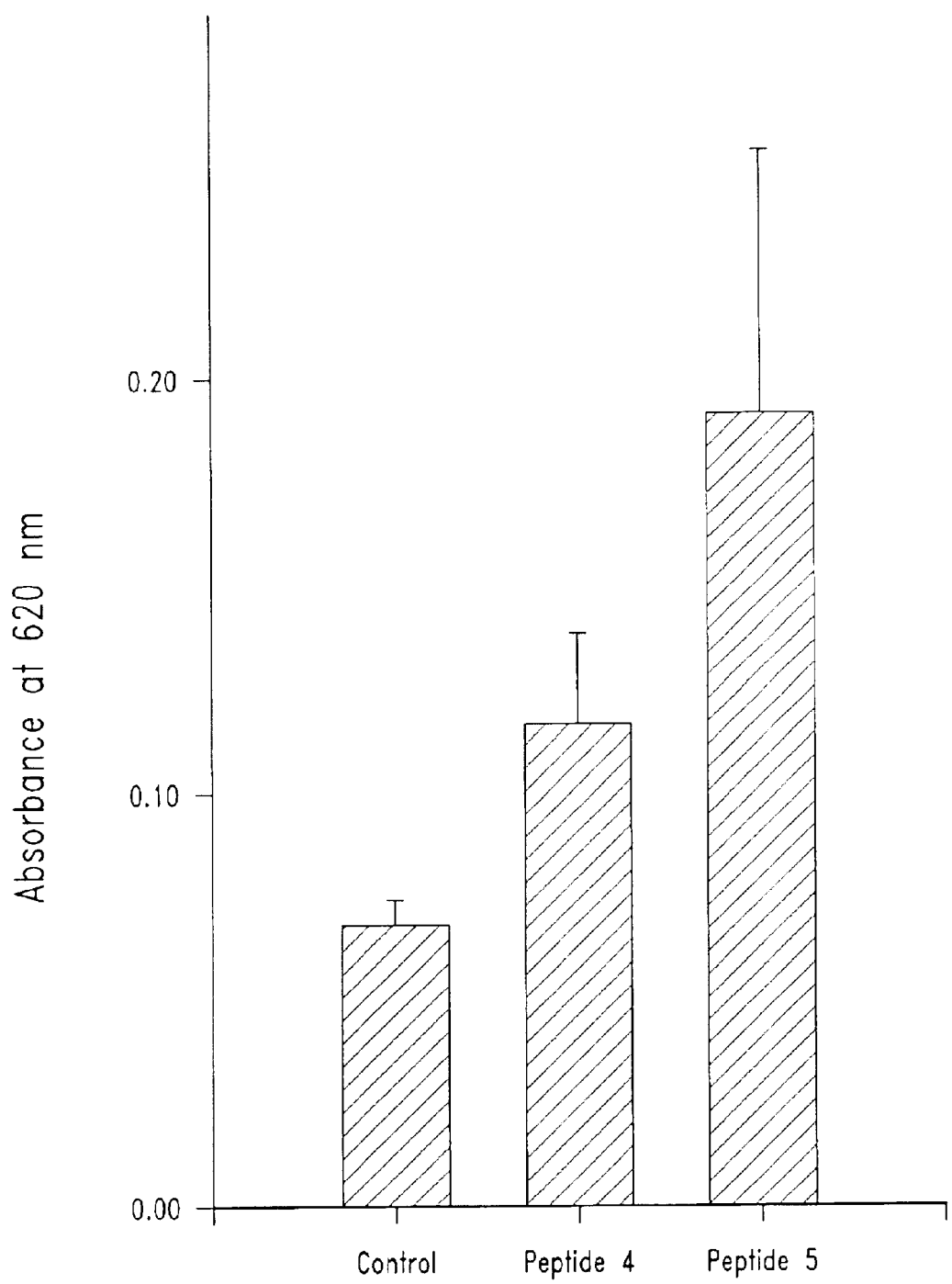
FIG. 8 is a histogram depicting the optical densities of dimethylformamide extracts prepared from the excised sites of the shaved back of a rat that received duplicate subdermal injections of either phosphate buffered saline, phosphate buffered saline containing acetyl-<u>CLYHYC</u>-NH$_2$ (SEQ ID NO:3; Peptide 4), or H-<u>CLYHYC</u>-OH (SEQ ID NO:3; Peptide 5) at a concentration of 100 µg/ml, followed 15 minutes later by a single injection of Evans blue into the tail vein.

The effects of injecting either phosphate buffered saline, phosphate buffered saline containing acetyl-CLYHYC-NH$_2$ (SEQ ID NO:3) or H-CLYHYC-OH (SEQ ID NO:3) into sites along the shaved back of a rat on the accumulation of Evans blue at the injection sites is shown in FIG. 7. FIG. 8 shows a histogram depicting the optical densities of dimethylformamide extracts prepared from the excised sites of the shaved back of a rat that received injections of either phosphate buffered saline, phosphate buffered saline containing acetyl-CLYHYC-NH$_2$ (SEQ ID NO: 3), or H-CLYHYC-OH (SEQ ID NO:3) at a concentration of 100 µg/ml, followed 15 minutes later by a single injection of Evans blue into the tail vein. Note that more dye was extracted from the sites injected with H-CLYHYC-OH (SEQ ID NO:3), than from sites injected with either phosphate buffered saline, or acetyl-CLYHYC-NH$_2$ (SEQ ID NO:3).

EXAMPLE 4

Effect of Representative Modulating Agents on Electrical Resistance Across Cell Monolayer This Example illustrates an electrical resistance assay for evaluating the effects of occludin-modulating agents on epithelial cell adhesion.

Madin Darby canine kidney (MDCK) cells were plated in Millicells (Millipore, Bedford, Mass.), at a density of 300,000 cells per Millicell, and cultured in Dulbecco's Modified Eagle Medium (DMEM; Sigma, St. Louis, Mo.) containing 5% fetal calf serum (Sigma, St. Louis, Mo.). Monolayers were exposed to the modulating agent dissolved in medium at a final concentration of 0.5 mg/ml for a period of 24 hours. The electrical resistance was measured using the EVOM device (World Precision Instruments, Sarasota, Fla.). At the time of measurement, fresh medium, with or without the modulating agent, may be added to the Millicells.

Figure 9:
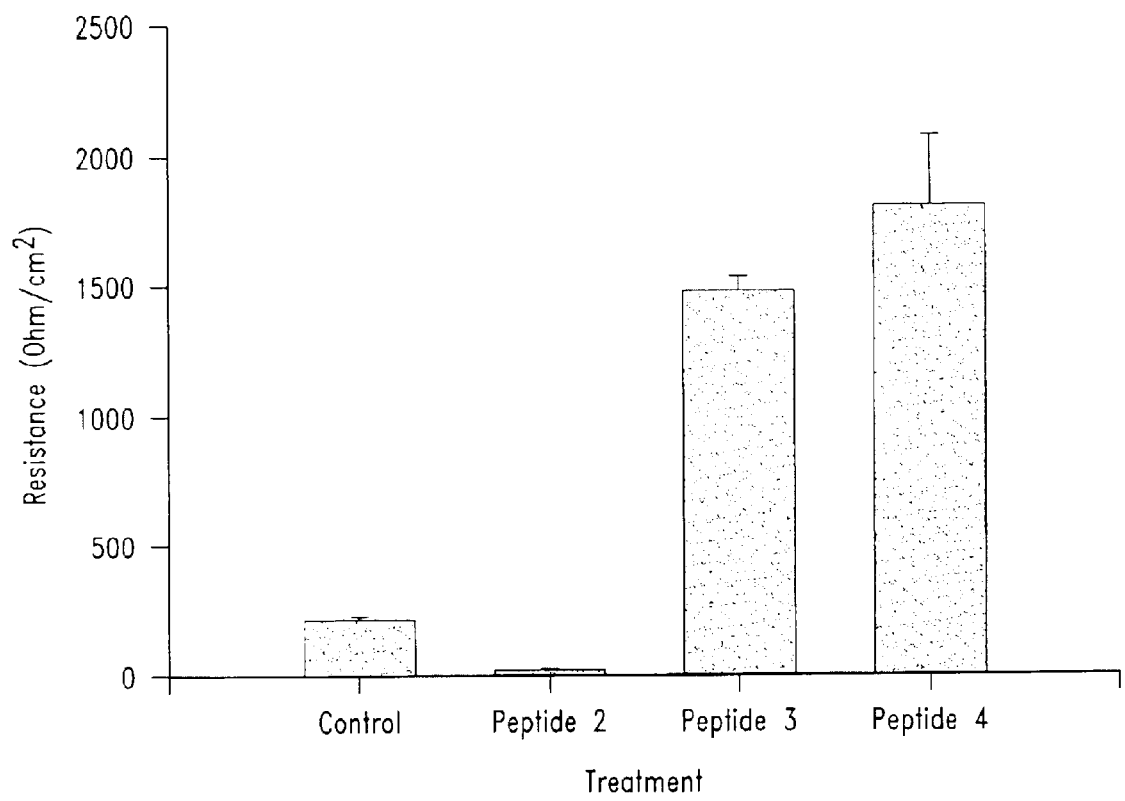
FIG. 9 is a histogram depicting the mean electrical resistance across MDCK cell monolayers cultured for 24 hours in medium alone (Control), or medium containing H-QYLYHYCVVD-NH$_2$ (Peptide 2), H-QYLYHYCVVD-COOH (Peptide 3) or N-Ac-<u>CLYHYC</u>-NH$_2$ (Peptide 4) at a concentration of 0.5 mg/ml. Duplicate measurements were taken, and error bars represent the standard deviation.

FIG. 9 is a histogram depicting the mean electrical resistance across MDCK cell monolayers cultured for 24 hours in medium alone (Control), or medium containing H-QYLYHYCVVD-NH$_2$ (SEQ ID NO:2; Peptide 2), H-QYLYHYCVVD-COOH (SEQ ID NO:2; Peptide 3) or N-Ac-CLYHYC-NH$_2$ (SEQ ID NO:3; Peptide 4) at a concentration of 0.5 mg/ml. Duplicate measurements were taken, and error bars represent the standard deviation. Peptide 2 was found to reduce the electrical resistance, while peptides 3 and 4 increased the electrical resistance across the monolayer, relative to the control. These results demonstrate the ability of occludin modulating agents to modulate the formation of tight junctions in epithelial cells. In particular, certain agents (such as peptides 3 and 4, above) stimulate the formation of tight junctions in epithelial cells.

EXAMPLE 5

Effect of Representative Modulating Agents on Neutrophil Migration on Endothelial Cells This Example illustrates the use of peptide modulating agents as provided herein to increase leukocyte infiltration into tumors.

Human umbilical vein endothelial cells (HUVEC) were harvested from umbilical cords by 0.2% collagenase treatment essentially as described by Yoshida et al., *Am. J. Physiol.* 262:H1891–1898, 1992. The cells were cultured in Endothelial Cell Growth Medium (EGM; Clonetics, San Diego, Calif.) supplemented with 10% heat-inactivated fetal calf serum (FCS; Hyclone, Logan, Md.), heparin sodium (10 IU/ml; Sigma, St. Louis, Mo.), 1 IU/ml penicillin, 1 mg/ml streptomycin, and 12.5 $\mu$g amphotericin B, and endothelial cell growth factor (80 ng/ml, Biomedical Technologies, Stoughton, Mass.). The cell cultures were incubated at 37° C. in a 100% humidified atmosphere with 5% $CO_2$ and expanded by brief trypsinization (0.25% trypsin in phosphate-buffer saline containing 0.02% EDTA. Primary passage HUVEC were seeded into fibronectin coated (5 $\mu$g/ml) tissue culture plates and used when confluent. Culture medium was replaced every second day. Only first-passage cultures were used for the studies. Cells were identified as endothelial cells by their cobblestone appearance at confluence, and by positive labeling with (1) acetylated low density lipoprotein labeled with Dil-Ac-LDL (Biomedical Technologies), and (2) mouse antihuman factor VIII (Calbiochem, San Diego, Calif.).

Human neutrophils (polymorphonuclear leukocytes, PMN) were isolated from venous blood of healthy adults using standard dextran sedimentation and gradient separation on Histoparque-1077 (Sigma) essentially as described by Harlan et al., *Lab. Invest.* 52(2):141–50, 1985. This procedure yielded a PMN population that was 95–98% viable (by trypan blue exclusion) and 98% pure (by acetic acid—crystal violet staining).

For neutrophil diapedesis experiments, HUVEC were grown to confluence on 8.0 $\mu$m pore cell culture inserts (Falcon, Franklin Lake, N.J.) essentially as described by Ohno et al., *inflammation* 21(3):313–24, 1997. Isolated neutrophils were suspended in PBS and radiolabeled by incubating PMN at $2 \times 10^7$ cells/ml with 30 $\mu$Ci $Na^{51}CrO_4$/ml (New England Nuclear, Natick, Mass.) at 37° C. for 60 minutes. The cells were then washed twice with cold phosphate-buffered saline (PBS), spun at 250 g for 8 minutes to remove unincorporated radioactivity and resuspended in PBS. The labeled neutrophils were added to the apical surface of HUVEC monolayers and allowed to migrate into the lower chamber for one hour. Migration assays were performed in the presence of $10^{-7}$ M N-formyl-methionyl-leucyl-phenylalanine (fMLP), a chemoattractant that causes the leukocytes to undergo diapedesis.

PMN migration was quantitated as follows:

$$\% \text{ Migration} = \frac{\text{Lower chamber (cpm)}}{[\text{Upper chamber (cpm)} + \text{lower chamber (cpm)}]}$$

Figure 10:
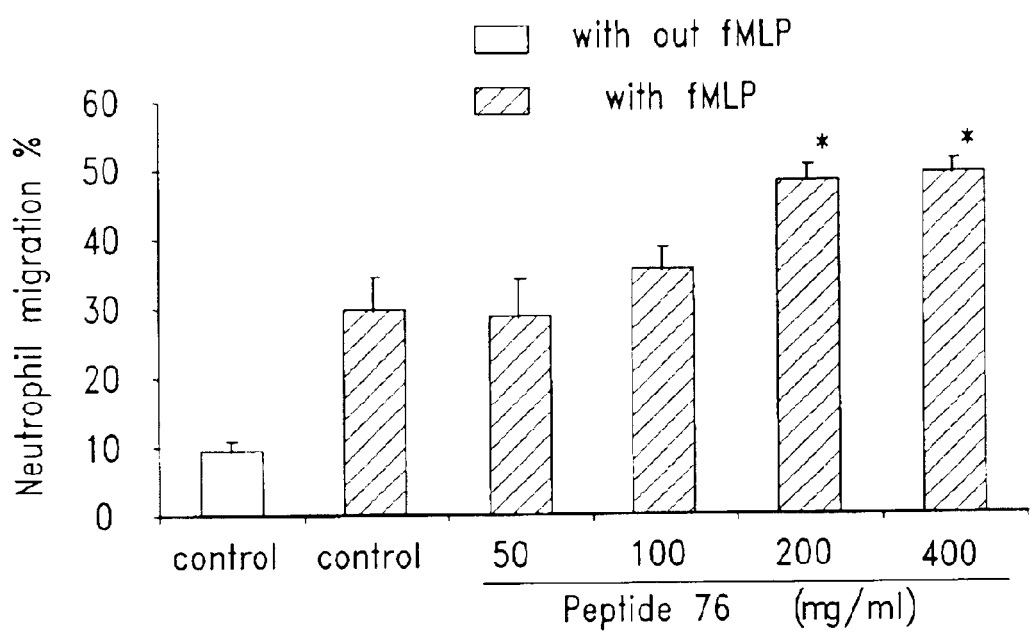
FIG. 10 is a graph illustrating the percent fMLP-stimulated migration for neutrophils in the presence of different levels of peptide 76 (H-<u>CLYHYC</u>-OH; SEQ ID NO:3), as indicated. Values presented are means±SE. *p<0.01 vs. control with fMLP.
Figure 11:
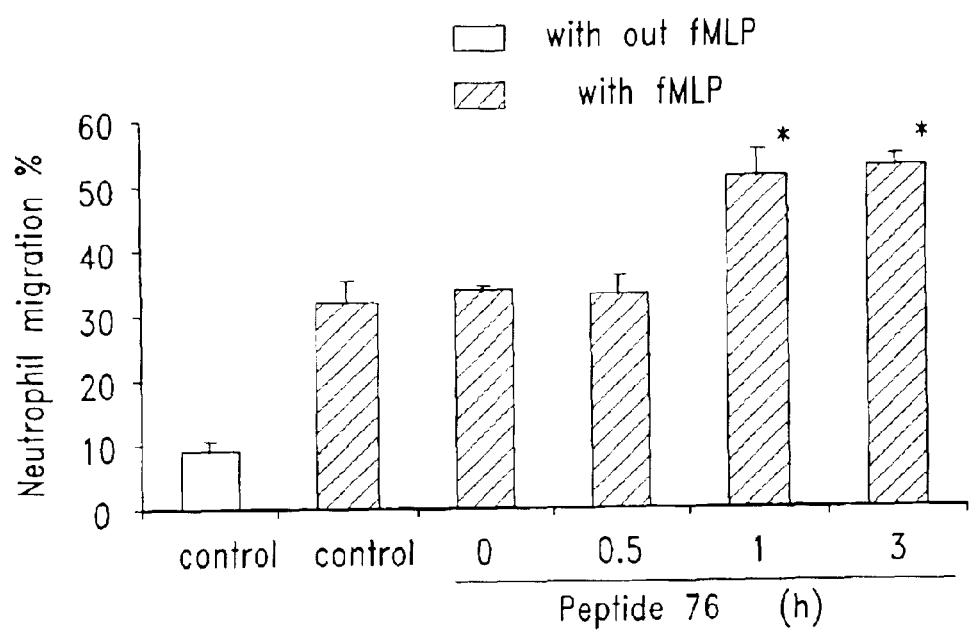
FIG. 11 is a graph showing the effect of peptide 76 (H-<u>CLYHYC</u>-OH; SEQ ID NO:3) on neutrophil migration over time, as indicated. Values presented are means±SE. *p<0.01 vs. control with fMLP. Data were analyzed using one-way ANOVA with Bonferroni's correction for multiple comparisons. Significance was accepted at p<0.05.
Figure 12A:
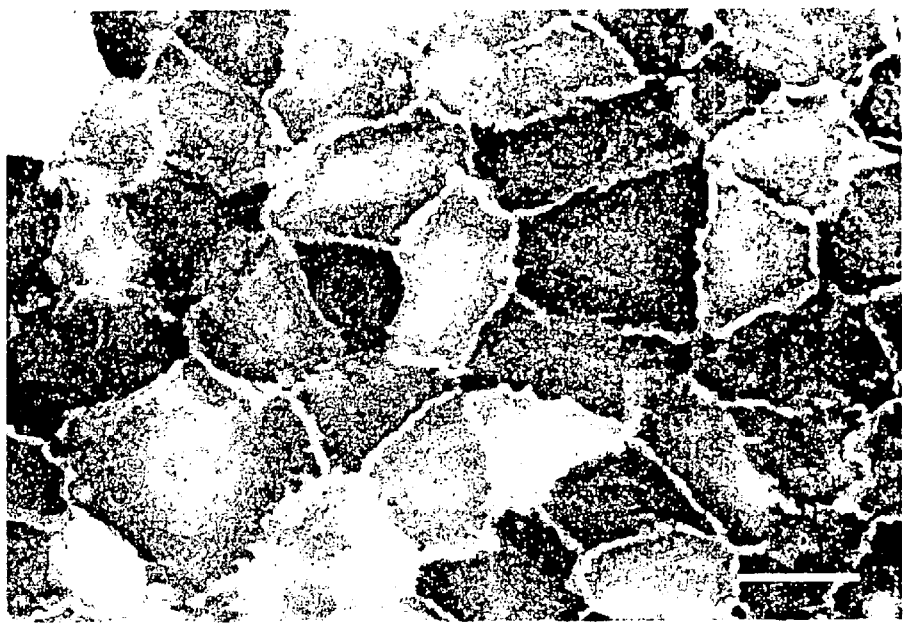
FIGS. 12A and 12B are photographs illustrating the results of immunofluorescence analysis of occludin in HUVEC grown on glass coverslips and treated with vehicle (FIG. 12A) or 200 µg/mL peptide 76 (FIG. 12B). Cells were fixed with methanol and acetone and stained for occludin. Immunofluorescent staining was performed with anti-occludin polyclonal antibody and Cy3-conjugated goat anti-rabbit secondary antibody, and analyzed by fluorescence microscope.
Figure 12B:
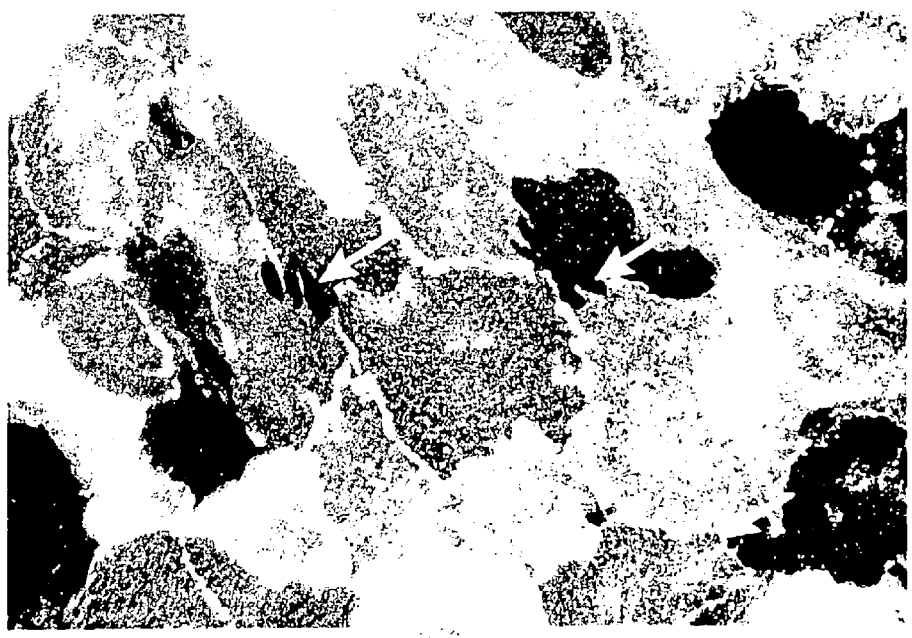

FIGS. 10–11 present the results of these experiments to evaluate the effect of modulating agents and control peptides on neutrophil transendothelial migration. In FIG. 10, the percent fMLP-stimulated migration is shown for neutrophils in the presence of different levels of peptide 76 (H-<u>CLYHYC</u>-OH; SEQ ID NO:3), as indicated. Values presented are means±SE. *p<0.01 vs. control with fMLP. FIG. 11 shows the effect of peptide 76 (H-<u>CLYHYC</u>-OH; SEQ ID NO:3) on neutrophil migration over time, as indicated. Values presented are means±SE. *p<0.01 vs. control with fMLP. Data were analyzed using one-way ANOVA with Bonferroni's correction for multiple comparisons. Significance was accepted at p<0.05. These results indicate that the representative modulating agent H-<u>CLYHYC</u>-OH (SEQ ID NO:3) can increase fMLP-stimulated transendothelial migration, For immunofluorescence analysis of occludin, HUVEC grown on glass coverslips were treated with vehicle (FIG. 12A) or 200 $\mu$g/mL peptide 76 (FIG. 12B). Cells were fixed with methanol and acetone and stained for occludin (Kevil et al., *Microcirculation* 5:197–210, 1998). Immunofluorescent staining was performed with anti-occludin polyclonal antibody (Zymed, San Francisco, Calif. used at a concentration of 4 $\mu$g/ml) and Cy3-conjugated goat anti-rabbit secondary Ab (Jackson Labs, Westgrove, Pa., used at a 1:250 dilution), and analyzed by fluorescence microscope. FIG. 12B shows the gaps between adjacent endothelial cells and the lack of junctional proteins at these gaps (arrows). The photographs shown are representative of at least 20 different fields observed in each experiment and of three independent experiments. Bar=25 $\mu$m.

EXAMPLE 6

Effect of Representative Modulating Agents on Transendothelial Permeability This Example illustrates the use of peptide modulating agents as provided herein to increase transendothelial permeability.

Endothelial barrier function was evaluated by measuring the transendothelial flux of FITC dextran using monolayers of human umbilical vein endothelial cells cultured to confluency on 8 $\mu$m pore transwell inserts (Falcon). The surface area of these inserts was 0.32 $cm^2$. The total volume for the medium inside of this insert was 0.5 ml. These inserts with cells were cultured inside of a 24 well tissue culture plate adapted for transwell inserts (Falcon) and the total volume in the 'outer' compartment was 1 ml. Cells were cultured to 100% confluency under these conditions in medium consisting of endothelial growth medium-2 (EGM-2, Biowhittaker) for 72 hours. Cells were used for solute flux protocols at this point.

Figure 13:
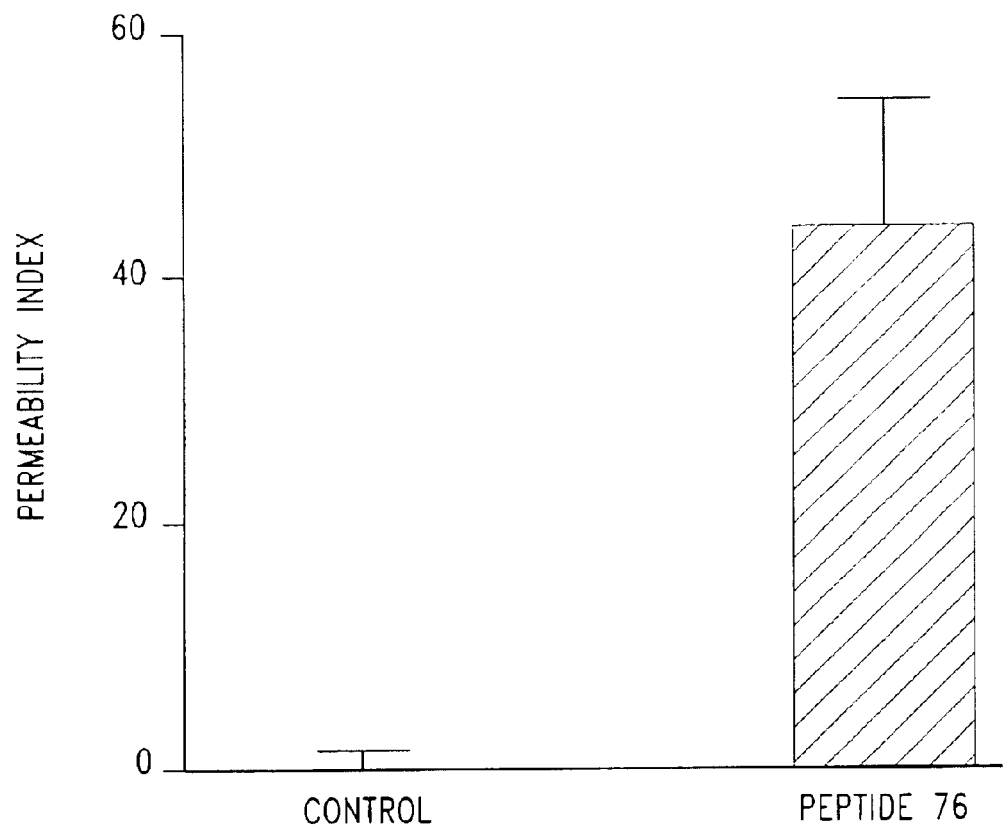
FIG. 13 is a histogram illustrating the effect of peptide 76 (H-<u>CLYHYC</u>-OH; SEQ ID NO:3) on transendothelial permeability. Values presented are means±SE.

To perform solute flux (permeability) measurements, monolayers were washed with Hank's balanced salts solution (HBSS) and incubated in either HBSS alone (control) or HBSS+peptide 76 (H-<u>CLYHYC</u>-OH; SEQ ID NO:3) at a concentration of 200 $\mu$g/ml for 60 minutes in peptide culture dishes. These chamber inserts were transferred to in the 'outer' compartment. FITC-dextran (10 kD) was added to the upper compartment to a final concentration of 0.45 mM (0.45%) and incubated at 37° C. for an additional 60 minutes. At the end of this incubation period, the insert was removed and 200 µl of the lower chamber contents aspirated and the absorbance measured spectrophotometrically. These experiments were performed such that n=4. Statistical significance was determined using one-way analysis of variance (ANOVA) with Bonferroni post testing to test for significance between groups. The results are presented in FIG. 13, which shows the ability of peptide 76 (H-CLYHYC-OH; SEQ ID NO:3) to increase transendothelial permeability.

From the foregoing, it will be evident that although specific embodiments of the invention have been described herein for the purpose of illustrating the invention, various modifications may be made without deviating from the spirit and scope of the invention.

What is claimed is:

1. A method for enhancing the delivery of a drug to a tumor in a mammal, comprising administering to said mammal a cell adhesion modulating agent and a drug, wherein said modulating agent comprises the sequence LYHY (SEQ ID NO:1), and wherein said modulating agent inhibits occludin-mediated cell adhesion.

2. A method for enhancing the delivery of a drug to a tumor in a mammal, comprising administering to said mammal a cell adhesion modulating agent and a drug, wherein said modulating agent comprises an antibody or fragment thereof that specifically binds to an occludin cell adhesion recognition sequence, and wherein said modulating agent inhibits occludin-mediated cell adhesion.

3. A method according to claim 1 or claim 2, wherein the tumor is selected from the group consisting of bladder tumors, ovarian tumors and melanomas.

4. A method according to claim 1 or claim 2, wherein said composition is administered to said tumor.

5. A method according to claim 1 or claim 2, wherein said composition is administered systemically.

6. A method according to claim 1, wherein said modulating agent comprises a sequence selected from the group consisting of QYLYHYCVVD (SEQ ID NO:2), YLYHY-CVVD (SEQ ID NO:12), LYHYCVVD (SEQ ID NO:13), QYLYHYC (SEQ ID NO:14), YLYHYC (SEQ ID NO:15), LYHYC (SEQ ID NO:16), QYLYHY (SEQ ID NO:17), YLYHY (SEQ ID NO:18), CLYHYC (SEQ ID NO:3), CLYHYC (SEQ ID NO:40), CQYLYHYC(SEQ ID NO:41), KQYLYHYD (SEQ ID NO:42), YLYHY(SEQ ID NO:43), QYLYHY (SEQ ID NO:44), and KLYHYD (SEQ ID NO:45).

7. A method according to claim 1 or claim 2, wherein said modulating agent is linked to said drug.

8. A method according to claim 1 or claim 2, wherein said modulating agent further comprises one or more of:

(a) a cell adhesion recognition sequence bound by an adhesion molecule other than an occludin, wherein said cell adhesion recognition sequence is separated from any LYHY (SEQ ID NO:1) sequence(s) by a linker; and/or (b) an antibody or antigen-binding fragment thereof that binds to a cell adhesion recognition sequence bound by an adhesion molecule other than an occludin.

9. A method according to claim 8, wherein said cell adhesion recognition sequence comprises one or more sequences selected from the group consisting of HAV, NQK, NRN, NKD, EKD, ERD, RGD, DDK, EEY, EAQ, IYSY (SEQ ID NO:49), TSSY (SEQ ID NO:50), VTAF (SEQ ID NO:51) and VSAF (SEQ ID NO:52).

10. A method according to claim 8, wherein said antibody or antigen-binding fragment thereof binds to a cell adhesion recognition sequence comprising a sequence selected from the group consisting of HAV, NQK, NRN, NKD, EKD, ERD, RGD, DDK, EEY, EAQ, IYSY (SEQ ID NO:49), TSSY (SEQ ID NO:50), VTAF (SEQ ID NO:51) and VSAF (SEQ ID NO:52).

11. A method according to claim 1 or claim 2, wherein said modulating agent and said drug are present within a pharmaceutical composition comprising a pharmaceutically acceptable carrier.

12. A method according to claim 11, wherein said pharmaceutical composition further comprises a modulator of cell adhesion comprising one or more of:

(a) a cell adhesion recognition sequence bound by an adhesion molecule other than an occludin; and/or (b) an antibody or antigen-binding fragment thereof that binds to a cell adhesion recognition sequence bound by an adhesion molecule other than an occludin.

13. A method according to claim 12, wherein said cell adhesion recognition sequence comprises one or more sequences selected from the group consisting of HAV, NQK, NRN, NKD, EKD, ERD, RGD, DDK, EEY, EAQ, IYSY (SEQ ID NO:49), TSSY (SEQ ID NO:50), VTAF (SEQ ID NO:51) and VSAF (SEQ ID NO:52).

14. A method according to claim 12, wherein said antibody or antigen-binding fragment thereof binds to a cell adhesion recognition sequence comprising a sequence selected from the group consisting of HAV, NQK, NRN, NKD, EKD, ERD, RGD, DDK, EEY, EAQ, IYSY (SEQ ID NO:49), TSSY (SEQ ID NO:50), VTAF (SEQ ID NO:51) and VSAF (SEQ ID NO:52).

15. A method for enhancing immune cell infiltration into a tumor in a mammal, comprising administering to a mammal a cell adhesion modulating agent and a drug, wherein said modulating agent comprises the sequence LYHY (SEQ ID NO:1), and wherein said modulating agent inhibits occludin-mediated cell adhesion.

16. A method for enhancing immune cell infiltration into a tumor in a mammal, comprising administering to a mammal a cell adhesion modulating agent and a drug, wherein said modulating agent comprises an antibody or fragment thereof that specifically binds to an occludin cell adhesion recognition sequence, and wherein said modulating agent inhibits occludin-mediated cell adhesion.

17. A method according to claim 15 or claim 16, wherein the tumor is selected from the group consisting of bladder tumors, ovarian tumors and melanomas.

18. A method according to claim 15 or claim 16, wherein said composition is administered to said tumor.

19. A method according to claim 15 or claim 16, wherein said composition is administered systemically.

20. A method according to claim 15, wherein said modulating agent comprises a sequence selected from the group consisting of QYLYHYCVVD (SEQ ID NO:2), YLYHYCVVD (SEQ ID NO:12), LYHYCVVD (SEQ ID NO:13), QYLYHYC (SEQ ID NO:14), YLYHYC (SEQ ID NO:15), LYHYC (SEQ ID NO:16), QYLYHY (SEQ ID NO:17), YLYHY (SEQ ID NO:18), CLYHYC (SEQ ID NO:3), CYLYHYC (SEQ ID NO:40), CQYLYHYC(SEQ ID NO:41), KQYLYHYD (SEQ ID NO:42), YLYHY(SEQ ID NO:43), QYLYHY (SEQ ID NO:44), KLYHYD and (SEQ ID NO:45).

21. A method according to claim 15 or claim 16, wherein said modulating agent and said drug are present within a pharmaceutical composition comprising a pharmaceutically acceptable carrier.

* * * * *

UNITED STATES PATENT AND TRADEMARK OFFICE
CERTIFICATE OF CORRECTION

PATENT NO.    : 6,797,807 B1                                             Page 1 of 1
DATED         : September 28, 2004
INVENTOR(S)   : Orest W. Blaschuk et al.

It is certified that error appears in the above-identified patent and that said Letters Patent is hereby corrected as shown below:

<u>Column 60,</u>
Line 47, "CLYHYC (SEQ ID NO:40)" should read as
-- CYLYHYC (SEQ ID NO:40) --.

Signed and Sealed this

Twenty-third Day of August, 2005

JON W. DUDAS
*Director of the United States Patent and Trademark Office*

SEQUENCE LISTING

```
<160> NUMBER OF SEQ ID NOS: 52

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  Occludin
      cell adhesion recognition sequence

<400> SEQUENCE: 1

Leu Tyr His Tyr
  1

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:  Cell
      adhesion modulating agent

<400> SEQUENCE: 2

Gln Tyr Leu Tyr His Tyr Cys Val Val Asp
  1               5                  10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:  Cell
      adhesion modulating agent
<220> FEATURE:
<223> OTHER INFORMATION: Cyclic peptide

<400> SEQUENCE: 3

Cys Leu Tyr His Tyr Cys
  1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: N-cadherin
      cell adhesion recognition sequence

<400> SEQUENCE: 4

Phe His Leu Arg Ala His Ala Val Asp Ile Asn Gly Asn Gln Val
  1               5                  10                  15

<210> SEQ ID NO 5
<211> LENGTH: 48
<212> TYPE: PRT
<213> ORGANISM: Homo sapiens
```

-continued

```
<400> SEQUENCE: 5

Gly Val Asn Pro Thr Ala Gln Ser Ser Gly Ser Leu Tyr Gly Ser Gln
 1               5                  10                  15

Ile Tyr Ala Leu Cys Asn Gln Phe Tyr Thr Pro Ala Ala Thr Gly Leu
            20                  25                  30

Tyr Val Asp Gln Tyr Leu Tyr His Tyr Cys Val Val Asp Pro Gln Glu
        35                  40                  45

<210> SEQ ID NO 6
<211> LENGTH: 48
<212> TYPE: PRT
<213> ORGANISM: Mus musculus

<400> SEQUENCE: 6

Gly Val Asn Pro Thr Ala Gln Ala Ser Gly Ser Met Tyr Gly Ser Gln
 1               5                  10                  15

Ile Tyr Met Ile Cys Asn Gln Phe Tyr Thr Pro Gly Gly Thr Gly Leu
            20                  25                  30

Tyr Val Asp Gln Tyr Leu Tyr His Tyr Cys Val Val Asp Pro Gln Glu
        35                  40                  45

<210> SEQ ID NO 7
<211> LENGTH: 48
<212> TYPE: PRT
<213> ORGANISM: Canis sp.

<400> SEQUENCE: 7

Gly Val Asn Pro Thr Ala Gln Ala Ser Gly Ser Leu Tyr Ser Ser Gln
 1               5                  10                  15

Ile Tyr Ala Met Cys Asn Gln Phe Tyr Ala Ser Thr Ala Thr Gly Leu
            20                  25                  30

Tyr Met Asp Gln Tyr Leu Tyr His Tyr Cys Val Val Asp Pro Gln Glu
        35                  40                  45

<210> SEQ ID NO 8
<211> LENGTH: 50
<212> TYPE: PRT
<213> ORGANISM: dipodomys sp.

<400> SEQUENCE: 8

Gly Val Asn Pro Arg Ala Gly Leu Gly Ala Ser Ser Gly Ser Leu Tyr
 1               5                  10                  15

Tyr Asn Gln Met Leu Met Leu Cys Asn Gln Met Met Ser Pro Val Ala
            20                  25                  30

Gly Gly Ile Met Asn Gln Tyr Leu Tyr His Tyr Cys Met Val Asp Pro
        35                  40                  45

Gln Glu
    50

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:
      Representative occludin cell adhesion recognition sequence

<400> SEQUENCE: 9

Leu Tyr His Tyr Leu Tyr His Tyr
     1               5
```

```
<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence:
      Representative occludin cell adhesion recognition sequence

<400> SEQUENCE: 10

Gln Leu Tyr His Tyr Gln Leu Tyr His Tyr Gln Leu Tyr His Tyr
 1               5                  10                  15

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Cell
      adhesion recognition sequence bound by N-cell adhesion molecules

<400> SEQUENCE: 11

Lys Tyr Ser Phe Asn Tyr Asp Gly Ser Glu
 1               5                  10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 12

Tyr Leu Tyr His Tyr Cys Val Val Asp
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 13

Leu Tyr His Tyr Cys Val Val Asp
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 14

Gln Tyr Leu Tyr His Tyr Cys
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Cell
      adhesion modulation agent
```

```
<400> SEQUENCE: 15

Tyr Leu Tyr His Tyr Cys
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 16

Leu Tyr His Tyr Cys
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 17

Gln Tyr Leu Tyr His Tyr
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 18

Tyr Leu Tyr His Tyr
 1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 19

Cys Asp Gly Tyr Pro Lys Asp Cys Lys Gly
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic Peptide

<400> SEQUENCE: 20

Cys Asp Gly Tyr Pro Lys Asp Cys Lys Gly
 1               5                  10

<210> SEQ ID NO 21
```

```
<211> LENGTH: 10
<212> TYPE: PRT
<213> ORGANISM: Artificial Sequence
<220> FEATURE:
<223> OTHER INFORMATION: Description of Artificial Sequence: Cell
      adhesion modulation agent

<400> SEQUENCE: 21

Cys Gly Asn Leu Ser Thr Cys Met Leu Gly
  1               5

<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 26

Cys Leu Tyr His Tyr Cys
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 27

Cys Gln Tyr Leu Tyr His Tyr Cys
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 28

Cys Gln Tyr Leu Tyr His Tyr Cys
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 29

Cys Tyr Leu Tyr His Tyr Cys
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 30

Cys Tyr Leu Tyr His Tyr Cys
 1               5

<210> SEQ ID NO 31
<211> LENGTH: 6
<212> TYPE: PRT

```
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide
<220> FEATURE:
<221> NAME/KEY: MOD_RES
<222> LOCATION: (6)
<223> OTHER INFORMATION: Where Xaa is beta,beta-dimethylcysteine

<400

```
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide
<220> FEATURE:
<221> NAME/KEY: MOD_RES
<222> LOCATION: (1)
<223> OTHER INFORMATION: beta,beta-pentamethylene-beta-mercaptopropionic
      acid

<400> SEQUENCE: 35

Xaa Leu Tyr His Tyr Cys
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 36

Lys Leu Tyr His Tyr Asp
 1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 37

Lys Gln Tyr Leu Tyr His Tyr Asp
 1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Cell
      adhesion modulation agent
<220> FEATURE:
<223> OTHER INFORMATION: Cyclic peptide

<400> SEQUENCE: 38

Trp Gly Gly Trp
 1

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: E-cadherin
      cell adhesion recognition sequence

<400> SEQUENCE: 39

Leu Phe Ser His Ala Val Ser Ser Asn Gly
 1               5                  10
```

```
<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Cell
      adhesion modulating agent
<220> FEATURE:
<223> OTHER INFORMATION: Cyclic peptide

<400> SEQUENCE: 40

Cys Tyr Leu Tyr His Tyr Cys
 1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence:  Cell
      adhesion modulating agent
<220> FEATURE:
<223> OTHER INFORMATION: Cyclic peptide

<400> SEQUENCE: 41

Cys Gln Tyr Leu Tyr His Tyr Cys
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Cell
      adhesion modulating agent
<220> FEATURE:
<223> OTHER INFORMATION: Cyclic Peptide

<400> SEQUENCE: 42

Lys Gln Tyr Leu Tyr His Tyr Asp
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:  Cell
      adhesion modulating agent
<220> FEATURE:
<223> OTHER INFORMATION: Cyclic peptide

<400> SEQUENCE: 43

Tyr Leu Tyr His Tyr
 1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence:  Cell
      adhesion modulating agent
<220> FEATURE:
<223> OTHER INFORMATION: Cyclic peptide

<400> SEQUENCE: 44

Gln Tyr Leu Tyr His Tyr
```

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Cell
      adhesion modulating agent
<220> FEATURE:
<223> OTHER INFORMATION: Cyclic peptide

<400> SEQUENCE: 45

Lys Leu Tyr His Tyr Asp
 1               5

<210> SEQ ID NO 46
<211> LENGTH: 51
<212> TYPE: PRT
<213> ORGANISM: Homo sapiens
<220> FEATURE:
<221> NAME/KEY: MOD_RES
<222> LOCATION: (8)
<223> OTHER INFORMATION: Where Xaa is any amino acid residue
<220> FEATURE:
<221> NAME/KEY: MOD_RES
<222> LOCATION: (17)
<223> OTHER INFORMATION: Where Xaa is any amino acid residue
<220> FEATURE:
<221> NAME/KEY: MOD_RES
<222> LOCATION: (22)..(23)
<223> OTHER INFORMATION: Where Xaa is any amino acid residue
<220> FEATURE:
<221> NAME/KEY: MOD_RES
<222> LOCATION: (29)
<223> OTHER INFORMATION: Where Xaa is any amino acid residue
<220> FEATURE:
<221> NAME/KEY: MOD_RES
<222> LOCATION: (31)
<223> OTHER INFORMATION: Where Xaa is any amino acid residue
<220> FEATURE:
<221> NAME/KEY: MOD_RES
<222> LOCATION: (37)
<223> OTHER INFORMATION: Where Xaa is any amino acid residue

<400> SEQUENCE: 46

Gly Val Asn Pro Thr Ala Gln Xaa Gly Ala Ser Ser Gly Ser Leu Tyr
 1               5                  10                  15

Xaa Ser Gln Ile Tyr Xaa Xaa Cys Asn Gln Phe Tyr Xaa Pro Xaa Ala
            20                  25                  30

Thr Gly Leu Tyr Xaa Asp Gln Tyr Leu Tyr His Tyr Cys Val Val Asp
        35                  40                  45

Pro Gln Glu
    50

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Claudin
      cell adhesion recognition sequence
<220> FEATURE:
<221> NAME/KEY: MOD_RES
<222> LOCATION: (2)
<223> OTHER INFORMATION: Where Xaa is either Lysine or Arginine
<220> FEATURE:
<221> NAME/KEY: MOD_RES
<222> LOCATION: (3)
<223> OTHER INFORMATION: Where Xaa is an independently selected amino
      acid residue

```
<220> FEATURE:
<221> NAME/KEY: MOD_RES
<222> LOCATION: (4)
<223> OTHER INFORMATION: Where Xaa is an independently selected amino
      acid residue
<220> FEATURE:
<221> NAME/KEY: MOD_RES
<222> LOCATION: (5)
<223> OTHER INFORMATION: Where Xaa is either Serine or Arginine
<220> FEATURE:
<221> NAME/KEY: MOD_RES
<222> LOCATION: (6)
<223> OTHER INFORMATION: Where Xaa is either tyrosine or phenylalanine
<220> FEATURE:
<221> NAME/KEY: MOD_RES
<222> LOCATION: (7)
<223> OTHER INFORMATION: Where Xaa is an independently selected amino
      acid residue

<400> SEQUENCE: 47

Trp Xaa Xaa Xaa Xaa Xaa Xaa Gly
 1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Non-
      classical cell adhesion recognition sequence
<220> FEATURE:
<221> NAME/KEY: MOD_RES
<222> LOCATION: (1)
<223> OTHER INFORMATION: Where Xaa is an independently selected amino
      acid residue
<220> FEATURE:
<221> NAME/KEY: MOD_RES
<222> LOCATION: (3)
<223> OTHER INFORMATION: Where Xaa is an independently selected amino
      acid residue
<220> FEATURE:
<221> NAME/KEY: MOD_RES
<222> LOCATION: (4)
<223> OTHER INFORMATION: Where Xaa is isoleucine, leucine or valine
<220> FEATURE:
<221> NAME/KEY: MOD_RES
<222> LOCATION: (5)
<223> OTHER INFORMATION: Where Xaa is aspartic acid, asparigine or
      glutamic acid
<220> FEATURE:
<221> NAME/KEY: MOD_RES
<222> LOCATION: (6)
<223> OTHER INFORMATION: Where Xaa is an independently selected amino
      acid residue
<220> FEATURE:
<221> NAME/KEY: MOD_RES
<222> LOCATION: (7)
<223> OTHER INFORMATION: Where Xaa is and idependently selected amino
      acid residue
<220> FEATURE:
<221> NAME/KEY: MOD_RES
<222> LOCATION: (8)
<223> OTHER INFORMATION: Where Xaa is serine, threonin or asparigine

<400> SEQUENCE: 48

Xaa Phe Xaa Xaa Xaa Xaa Xaa Xaa Gly
 1               5

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence:
      Representative claudin cell adhesion recognition sequence
```

```
<400> SEQUENCE: 49

Ile Tyr Ser Tyr
 1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence:
      Representative claudin cell adhesion recognition sequence

<400> SEQUENCE: 50

Thr Ser Ser Tyr
 1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence:
      Representative claudin cell adhesion recognition sequence

<400> SEQUENCE: 51

Val Thr Ala Phe
 1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence:
      Representative claudin cell adhesion recognition sequence

<400> SEQUENCE: 52

Val Ser Ala Phe
 1
```